US011038969B2

(12) United States Patent
Subramaniam et al.

(10) Patent No.: US 11,038,969 B2
(45) Date of Patent: Jun. 15, 2021

(54) PLATFORM INDEPENDENT REALTIME MEDICAL DATA DISPLAY SYSTEM

(71) Applicant: Murata Vios, Inc., Woodbury, MN (US)

(72) Inventors: Ganesh Subramaniam, Bangalore (IN); Ebith Bersingh Lawrence, Kerala (IN); Ramakrishna Kapila Venkata, Vijayawada (IN)

(73) Assignee: MURATA VIOS, INC., Woodbury, MN (US)

( * ) Notice: Subject to any disclaimer, the term of this patent is extended or adjusted under 35 U.S.C. 154(b) by 0 days.

(21) Appl. No.: 16/710,555

(22) Filed: Dec. 11, 2019

(65) Prior Publication Data

US 2020/0204631 A1 Jun. 25, 2020

Related U.S. Application Data

(60) Provisional application No. 62/782,455, filed on Dec. 20, 2018.

(51) Int. Cl.
*H04L 29/08* (2006.01)
*G16H 10/60* (2018.01)
(Continued)

(52) U.S. Cl.
CPC .......... *H04L 67/141* (2013.01); *G06F 16/986* (2019.01); *G16H 10/60* (2018.01);
(Continued)

(58) Field of Classification Search
CPC ....... H04L 67/141; H04L 67/02; H04L 67/26; H04L 67/32; G16H 40/67; G16H 10/60; G06F 16/986
See application file for complete search history.

(56) References Cited

U.S. PATENT DOCUMENTS 5,371,842 A * 12/1994 Easton ............... G01R 13/0227
345/440
8,896,195 B2 11/2014 Dou
(Continued)

FOREIGN PATENT DOCUMENTS

WO WO 2014144339 9/2014
WO WO 2017218587 12/2017

OTHER PUBLICATIONS

International Search Report and Written Opinion in PCT Appln. No. PCT/US2019/067650, dated Apr. 8, 2020, 13 pages.
(Continued)

*Primary Examiner* — Christopher B Robinson
(74) *Attorney, Agent, or Firm* — Keating & Bennett, LLP

(57) ABSTRACT

A system for providing realtime medical data to a client device regardless of a type of a client device's platform. The system uses different types of connections to establish a connection between the client device and the system and to transfer realtime medical data between the client device and the system. For example, a Hypertext Transfer Protocol (HTTP) connection can be used to establish a connection between the client device and the system and a websocket connection can be used to transfer realtime medical data between the client device and the system. By using an HTTP connection, the system can initially establish a connection between the system and any client device compatible with an HTTP connection.

20 Claims, 10 Drawing Sheets

(51) Int. Cl.
*G16H 40/67* (2018.01)
*G06F 16/958* (2019.01)

(52) U.S. Cl.
CPC ............. *G16H 40/67* (2018.01); *H04L 67/02* (2013.01); *H04L 67/26* (2013.01); *H04L 67/32* (2013.01)

(56) References Cited

U.S. PATENT DOCUMENTS

| | | |
|---|---|---|
| 2001/0044823 A1 | 11/2001 | Labounty |
| 2010/0030577 A1 | 2/2010 | Lawson |
| 2010/0082372 A1 | 4/2010 | Wen |
| 2015/0067021 A1* | 3/2015 | Protas .................... G16H 40/67 709/202 |
| 2015/0137968 A1 | 5/2015 | Rusin et al. |
| 2015/0142464 A1* | 5/2015 | Rusin .................... G16H 40/67 705/2 |
| 2015/0142475 A1 | 5/2015 | Rusin et al. |
| 2016/0063191 A1* | 3/2016 | Vesto .................... G16H 50/50 705/2 |
| 2017/0193182 A1 | 7/2017 | Mihai |
| 2020/0082930 A1* | 3/2020 | De Francesco ........ G16H 40/20 |

OTHER PUBLICATIONS

Lomotey and Deters, "Efficient Mobile Services Consumption in mHealth," 20123 IEEE/ACM International Conference on Advances in Social Networks Analysis and Mining, Aug. 25-29, 2013, pp. 982-989.

* cited by examiner

PLATFORM INDEPENDENT REALTIME MEDICAL DATA DISPLAY SYSTEM

CROSS-REFERENCE TO RELATED APPLICATION

This application claims the benefit of U.S. Provisional Application 62/782,455, filed on Dec. 20, 2018, the contents of this aforementioned application being fully incorporated herein by reference.

BACKGROUND

Patient treatment experiences within hospitals and other healthcare facilities can vary in numerous ways, including differences in initial interaction between a patient and caregivers, diagnosis, progression of treatment, physical movement of a patient within a facility, length of stay, recovery, and rehabilitation. For example, in some cases, a patient initiates interaction with a hospital by arriving at an emergency room to have an immediate need (such as an injury, heart failure, sudden pain, or other sudden health emergency) addressed by the hospital staff. From there, the patient may be rushed into surgery, scheduled for surgery at a later time, given one or more medications, scheduled for a later diagnostic consultation, treated and released, removed to an intensive care unit, moved to a recovery ward, or any other myriad actions could be taken with respect to the patient. As another example, in some cases, a patient initiates interaction with a hospital by scheduling a surgical procedure. In such a scenario, the patient may, for example, arrive at the hospital, be prepped for surgery, undergo the surgical procedure, spend an amount of time in a recovery ward, and then be moved to a general hospital ward before being released from the hospital and sent home.

In many cases, one or more surgical procedures make up part of a treatment plan for a patient. There are multiple environments that patients can be transitioned through after a surgical procedure. Immediately after a procedure, patients are gradually brought back to a stable condition, after which they are discharged to the home or a long-term care setting. The initial recovery process starts in the Intensive Care Unit (ICU) for patients requiring 24/7 clinician oversight. An ICU has the necessary equipment to monitor patient status and high staffing ratios to aid patient recovery. This environment can be very expensive for patients, as it is often the highest per-day cost out of any room in the hospital—leaving this environment as soon as possible is beneficial as it minimizes overall cost. For hospitals that are built around critical-care, ICU patient throughput is a highly scrutinized metric for the efficiency of their overall operations—it is the hospital's most expensive environment to staff and resource, and keeping patients there longer than necessary means another patient must wait for a bed to become available prior to receiving treatment. The transition of patients out of the ICU is therefore preferred for both hospitals and patients, but the risks associated with premature discharge often prevents early release of a patient.

While a patient is located in the ICU, basic vital sign data needed to determine patient stability are measured, recorded, tracked, and trended, a process which can often be clinical staff dependent, and which can restrict a clinician to a particular physical location where they can monitor patients and review vital signs and other data in person (e.g., by viewing a bedside ECG display that utilizes sensors connected to a patient). Patient vital signs that are collected can include: blood pressure, body temperature, respiratory rate, blood oxygenation, heart rhythm (via ECG), and heart rate. Along with this, there are soft metrics also used such as patient responsiveness and visual assessment.

In some cases, the recovery process can include moving a patient to a recovery room, either directly after surgery, or after a period of time spent in an ICU. As with ICUs, patient monitoring within a recovery room environment also includes a heavy reliance on clinician interpretation of any data that is generated, and this data may or may not be easily available to the original physician overseeing the patient's recovery.

From an ICU or recovery room, a patient can often be moved to a general ward. General wards often include lower caregiver to patient staffing ratios and less or no vital sign monitoring. In many cases, vital signs are often not monitored on a near constant basis, but rather nurses will make rounds to measure key vital signs. Additionally, such vital sign measurement can often be limited to a few basic parameters such as body temperature and blood pressure. After the general ward, the next phase in patient recovery progression is often discharge of the patient. It is generally considered best for patients to reach home and recover in this more comfortable environment as soon as possible. Being released from a hospital to continue recovery at home can minimize the risk of contracting unrelated in-hospital complications, and can better allow family members to aid with recovery, at lower-cost to the patient.

During the management of patients in multiple in-hospital and out-of-hospital environments, various stakeholders (human and non-human) are interested in consuming realtime medical data associated with patient status and the care received. These realtime medical data are often resident in disparate human and non-human sources, and are communicated to stakeholders through various modalities. Furthermore, coordinating care in a patient-centric manner is difficult as many stakeholders are continuously changing.

TECHNICAL FIELD

This invention relates to a system providing realtime medical data.

SUMMARY

This specification describes methods, systems, and computer-readable media for providing realtime medical data that are obtained from a monitoring device to a client device. In particular, the system can provide realtime medical data to a client device regardless of a type of a client device's platform. The system uses different types of connections to establish a connection between the client device and the system and to transfer realtime medical data between the client device and the system. For example, a Hypertext Transfer Protocol (HTTP) connection can be used to establish a connection between the client device and the system and a websocket connection can be used to transfer realtime medical data between the client device and the system. By using an HTTP connection, the system can initially establish a connection between the system and any client device compatible with an HTTP connection.

In general, one innovative aspect of the subject matter described in this specification can be implemented in a method performed, for example, by a computing system having one or more computers executing computer instructions stored on one or more non-transitory computer storage devices. The method can include receiving, by a service broker from a client device through a Hypertext Transfer Protocol (HTTP) connection, a first request for a web page, the first request including patient information for a particular patient; in response to the first request, determining, by the service broker, a particular web page based on the patient information for the particular patient, the particular web page displaying a first user interface; providing, by the service broker to the client device through the HTTP connection, the particular web page to establish a websocket connection between the service broker and the client device; establishing the websocket connection between the service broker and the client device; receiving, by the service broker from the client device through the websocket connection, a second request for first real time medical data, the second request identifying a medical data protocol that defines one or more data attributes for the first real time medical data; obtaining, by the service broker from one or more data sources, a first set of real time medical data samples that includes respective values of the one or more attributes for the first real time medical data; generating the first real time medical data based on the values of the one or more data attributes for the first real time medical data; and providing, by the service broker to the client device through the websocket connection, a second user interface to present the first real time medical data.

The method can optionally include one or more of the following features. In response to loading the particular web page on the client device, the particular web page can be configured to invoke the client device to establish the websocket connection between the client device and the service broker. Establishing the websocket connection between the service broker and the client device can include receiving, by the service broker from the client device, a websocket connection request that is invoked in response to loading the particular web page on the client device; and in response to the websocket connection request, providing, by the service broker to the client device a websocket connection response to establish the websocket connection between the service broker and the client device. The method can further include pushing, by the service broker to the client device, medical data asynchronously through the web socket connection.

Generating the first real time medical data based on the values of the values of the one or more data attributes for the first real time medical data can include identifying, by the service broker, respective values for an identification, a sample rate, a plot time, and buffer information from the second request including the respective values of the one or more data attributes for the first real time medical data, based on the value of the identification, determining a particular waveform of one or more waveforms that are monitored by a monitoring device in real time, based on the respective values of the plot time, the sample rate, and the buffer information, writing, by the service broker, the particular waveform in a buffer using the sampling rate for the plot time, and based on the particular waveform written in the buffer, generating, by the service broker, the first real time medical data.

The method can further include storing the generated first real time medical data in a database. Providing the first real time medical data can include reading, by the service broker, the first real time medical data stored in the database, and providing, by the service broker to the client device, the first real time medical data through the websocket connection. The client device can be a subscriber to the service broker for medical data. The websocket connection can be established between the service broker and the client device using communications based on Hypertext Markup Language (HTML).

The particular web page can simultaneously display (i) the first user interface provided from the service broker to the client device through the HTTP connection and (ii) the second user interface that presents the first real time medical data provided from the service broker to the client device through the websocket connection. The method can further include receiving, by the service broker from the client device through the websocket connection, a third request for second real time medical data, the third request including respective values of the one or more data attributes for the second real time medical data; receiving, by the service broker from the one or more data sources, a second set of real time medical data samples; generating the second real time medical data from the second set of real time medical data samples based on the values of the one or more data attributes for the second real time medical data; and updating, by the service broker, the second user interface to present the second real time medical data instead of the first real time medical data while maintaining the first user interface.

The subject matter described in this specification can be implemented in particular implementations and can result in one or more of the following advantages. A conventional system uses the same type of connection to establish a connection between a client device and the conventional system and to transfer realtime medical data between the client device and the conventional system. In comparison, a system described in this specification uses different types of connections to establish a connection between a client device and the system and to transfer realtime medical data between the client device and the system. In particular, by using a versatile type of connection, e.g., an HTTP connection, to establish a connection between the client device and the system, the system can establish a data connection to any client device that is compatible with the connection type regardless of the client device's platform. Thus, the system improves the compatibility and the flexibility to manage realtime medical data by allowing caregivers and other interested parties to review realtime medical data collected from patients using a standard interface (e.g., a web browser) on a remote computing device. The system provides data integrity without the need for a specialized application.

Moreover, the system does not require additional brokers to establish a connection between the client device and the system. This reduces the number of network devices in the entire network such that less network resources can be used to transfer the same data between the system and the client device. Thus, network resources can be used efficiently.

Furthermore, a conventional system requires a new connection between a client device and the conventional system whenever transferring realtime medical data. Thus, even if a connection was established before, a new connection should be established to transfer new realtime medical data. In comparison, the system described herein does not require any subsequent connection process to transfer realtime medical data once a connection to transfer realtime medical data is established between the system and the client device, Thus, the system uses less network resources comparing to the conventional system.

The subject matter described in this specification can be implemented so as to realize one or more of the following advantages. Compared to a conventional system, the disclosed techniques are more efficient. The disclosed system determines whether a current deployment manifest deployed in a deployment system is outdated and provides a notification, to a client device, indicating whether the current deployment manifest is outdated. In response to the notification, a determination as to whether the current deployment manifest should be upgraded or when the current deployment manifest is upgraded can be made. As a result, the system can avoid downtime by upgrading service implementations while the system is not performing other tasks or the system is not busy. Thus, the system can perform the upgrade to the service implementations efficiently.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTIONS OF DRAWINGS

Like reference numbers and designations in the various drawings indicate like elements.

DETAILED DESCRIPTION

Figure 1:
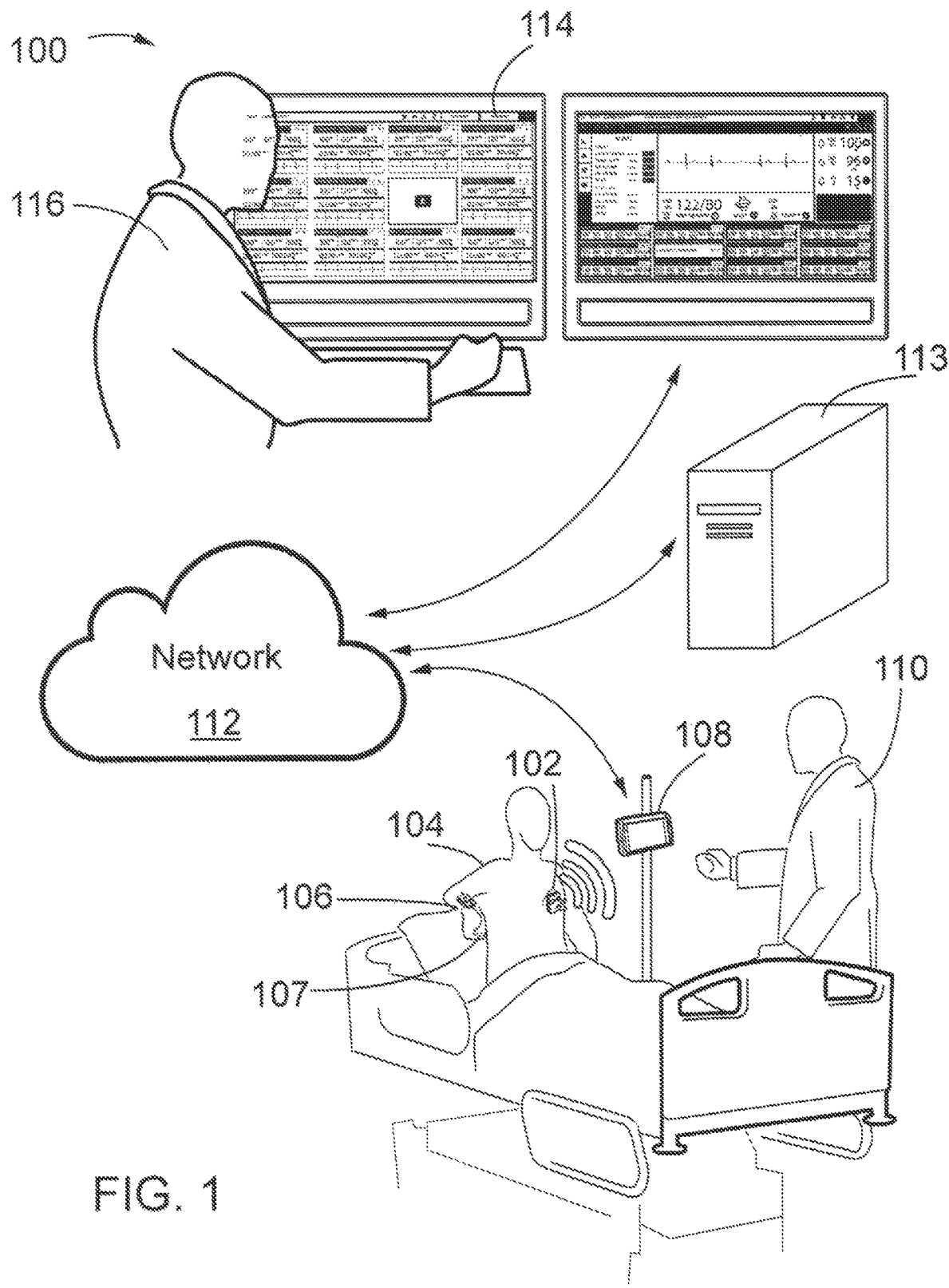
FIG. 1 is a diagram illustrating an example system for tracking and monitoring information associated with a patient.

FIG. 1 is a diagram illustrating an example system 100 for tracking and monitoring information associated with a patient. The system 100 can be used to monitor patient vital signs, track patient activity, track patient movement, record information associated with a patient, coordinate patient care, and provide up-to-date information to health care providers. The system 100 includes one or more monitoring devices, e.g., monitoring devices 102, 106, 107, and 108, a service broker, e.g., a service broker 113, and a client device, e.g., a client device 114.

Monitoring devices detect and record medical data for a patient. For example, the monitoring devices can detect and record various vital signs and other information for a patient. In some implementations, the monitoring devices include patient worn sensors. For example, the patient worn sensors can include a chest sensor 102 affixed to the chest of a patient 104 for tracking various vital signs of the patient 104. The patient worn sensors can additionally include a wrist sensor 106, which in the example shown is affixed to the patient 104's right wrist, but in practice could be affixed to either wrist of the patient 104. The patient worn sensors can interact with other components of the system 100 to identify alarm states for the patient 104. Alarm states can include various medical states or medical emergencies for the patient that may or may not require intervention by one or more caregivers. In some implementations, alarm states can be identified based on deviation of one or more vital signs or other metrics for the patient 104 outside of an acceptable range. Detection of an alarm state or other issue associated with the patient 104 or components of the system 100 that requires attention can result in one or more components of the system issuing an alert. An alert can take the form of information regarding an alarm state or other issue being displayed by a computing device, a notification sent to one or more caregivers, an audio alarm, a visual alarm, a tactile alarm (such as vibration), or another indicator.

The chest sensor 102 can include several adherent electrodes for contacting the skin of the patient 104 to record various vital signs for the patient, including heart rhythm (via ECG) and heart rate. The chest sensor 102 can be, for example, a 6-lead ECG sensor having I, II, III, aVL, aVR, and aVF leads. Other vital signs that can be monitored by the chest sensor 102 or a combination of the chest sensor 102 and the wrist sensor 106 can include blood pressure, body temperature, respiratory rate, blood oxygenation, blood glucose level, hydration levels and perspiration. In some implementations, the chest sensor 102 can include a reusable or permanent portion as well as disposable portions. For example, the chest sensor 102 can include a permanent housing for storing electrical components for processing signals received from and detected in association with the patient and for transmitting information to other devices. The chest sensor 102 can further include a disposable adherent electrode pad designed to affix to the chest of the patient 104. Electrodes included as part of the disposable adherent electrode pad can be configured to contact electrical leads of the permanent housing to convey signals from the patient 104 to the electrical components within the chest sensor 102. In some implementations, the permanent housing can include snap connectors for engaging electrodes of the disposable adherent electrode pad and for securing the disposable adherent electrode pad to the permanent housing. The disposable adherent electrode pad can be periodically removed and replaced with a fresh disposable adherent electrode pad while allowing many of the components of the chest sensor 102 to be continually reused.

The chest sensor 102 can also include sensors for detecting bio-impedance in order to monitor hydration levels, body fat levels, or other fluid levels for the patient 104. In some implementations, the chest sensor 102 can include electronics for processing and analyzing vital sign information and other information collected from the patient 104. In some implementations, the chest sensor 102 and/or other patient worn sensors collect raw, pre-processed information which is then transmitted to other portions of the system 100 for further processing and analysis.

In some implementations, the chest sensor 102 includes a temperature sensor that extends from a main body of the chest sensor 102 to underneath the patient 104's armpit for monitoring, tracking, and recording body temperature for the patient 104. The temperature sensor can include both reusable portions and temporary/disposable portions. For example, the temperature sensor can include a disposable contact for affixing to the patient 104's skin under the patient 104's armpit. The temperature sensor can, for example, further include permanent portions that include temperature sensing portions, circuitry for interpreting and processing temperature data received from the patient, and a cable running from the main body of the chest sensor 102 around the chest of the patient 104 to the patient 104's armpit. In some implementations, rather than including functionality for interpreting temperature data collected from the patient 104, the temperature sensor can collect raw data that is processed by circuitry contained within the main housing of the chest sensor 102 or other portions of the system 100.

In some implementations, the chest sensor 102 includes one or more accelerometers for detecting and recording patient motion, activity, position, and posture. For example, an accelerometer included within the chest sensor 102 can track patient activity to allow a caregiver to determine if the patient 104 is receiving a sufficient level of daily exercise, or if the patient 104 is engaging in too much activity for the current physical condition of the patient 104. The accelerometer can also be used to determine if the patient 104 has fallen, or if the patient 104 has been motionless for a specified period of time. For example, the accelerometer can determine that the patient has been in a particular posture for more than a specified time period, which can allow the system 100 to identify an alarm state for the patient and send out one or more alerts to elicit a caregiver response to the patient's alarm state. The accelerometer can also be used to track patient sleep patterns, or to track the posture of the patient 104 to allow caregivers to provide recommendations for how the patient 104 can better position himself when seated, lying, standing, etc. The accelerometer could additionally provide information to caregivers that can be used to determine if the patient 104 is engaging in activities or habits that can increase the risk of re-injury or of developing complications.

The chest sensor 102 can also include circuitry and components for identifying a physical location of the patient 104. For example, the chest sensor 102 can include a GPS unit or a radio signal triangulation based location determination device. A GPS unit or other location determination circuitry included within the chest sensor 102 can be used, for example, to identify a location of a patient when the patient is not located where the patient should be at a specified time. The GPS unit can be used to locate patients suffering from dementia or other mental illnesses who are prone to wandering and becoming lost. As another example, if the accelerometer in the chest sensor 102 determines that the patient 104 has fallen, the chest sensor 102 can transmit an alert to one or more caregivers that includes the location of the patient 104 to allow the caregivers to more easily determine where the patient 104 has fallen and attend to the patient 104's needs quickly and effectively.

Other components that can be included as part of the chest sensor 102 include a power supply, buttons or other input mechanisms for receiving user input, one or more audible alarms or speakers, and display lights or a display screen. A power supply for the chest sensor 102 can take the form of a battery pack for receiving standard disposable batteries, a rechargeable battery, or a removable battery pack that can be replaced with a fully charged battery pack. The chest sensor 102 can further include input mechanisms such as, for example, buttons, keys, or a touch screen. The input mechanisms can allow the patient 104 or a caregiver to adjust settings for the chest sensor 102, perform various tests (such as sensor tests, battery power level tests, etc.) or reset one or more alarms for the chest sensor 102. For example, the patient 104 or a caregiver can silence an audible alarm of the chest sensor 102 or stop a flashing light alarm of the chest sensor 102 by pressing a button on the chest sensor 102.

The chest sensor 102 can also include one or more audible alarms or speakers. Speakers or other noise emittance units included as part of the chest sensor 102 can provide an audible alarm when a particular patient event occurs. In some implementations, different types of audible alarms can indicate different patient events. For example, a first alarm sound can indicate cardiac arrest while a second alarm sound can indicate that the patient 104 has fallen and a third alarm can indicate irregular respiration for the patient 104. In some implementations, buttons or other input devices of the chest sensor 102 can be used to pause or reset an audible or visual alarm. The chest sensor 102 can also include display lights, a display screen, or other display mechanisms. For example, one or more LED lights can indicate a current status of one or more vital signs of the patient 104 or a current status of one or more components of the chest sensor 102. For example, an LED can indicate that a battery of the chest sensor 102 is low, while another LED can indicate that a communications unit (e.g., wireless Bluetooth communication circuitry) is malfunctioning. As yet another example, a display screen included as part of the chest sensor 102 can provide indications of one or more vital signs or other information collected by the chest sensor 102. For example, a display screen can show one or more ECG readings for the patient 104.

In some implementations, buttons or other input devices of the chest sensor can allow the patient 104 to initiate a patient distress call. For example, the patient 104 can select a button on the chest sensor 102 which can cause the chest sensor 102 to communicate a distress signal to a bedside monitor 108, or to another computing device using wireless communications and/or by communicating through a network 112. For example, when the patient 104 presses the button, the chest sensor 102 can transmit a distress signal to a computer located at a nursing station. The nursing station can then indicate to a caregiver that the patient 104 has initiated a distress call. Additionally, information related to the distress call can be recorded and stored along with an indication of a time when the distress call was made, and vital sign and other information for the patient at the time of the distress call.

In some implementations, one or more input devices of the chest sensor 102 can initiate microphone functionality of the chest sensor 102. For example, the patient 104 can select a button on the chest sensor 102 to activate a microphone included in the chest sensor 102. The microphone can allow the patient 104 to make an audio recording to, for example, indicate symptoms currently being experienced, or recently experienced by the patient 104. The audio recording can be recorded along with a time stamp of when the recording was made and stored in computer memory of the chest sensor 102 and/or another computing device in communication with the chest sensor 102. The audio recording (e.g., that includes the patient 104 reciting symptoms) can be used by one or more caregivers in diagnosing the patient 104.

In some implementations, the microphone functionality of the chest sensor 102 can be used to facilitate one-way or two-way audio communication between the patient 102 and a caregiver located at a different location. For example, the patient 104 can select a button of the chest sensor 102 to activate the microphone of the chest sensor 102 and initiate a two-way audio communication session with a caregiver located at a computing device at a different physical location than the patient 104 and the chest sensor 102. For example, the patient 104 can talk to a nurse located at a nursing station on the same floor of a hospital as the patient 104 to communicate problems, symptoms, or other information to the nurse. The nurse can communicate back to the patient 104. For example, the chest sensor 102 can include a speaker to emit audio transmitted by the nursing station to allow the nurse to provide instructions or comfort to the patient 104, or to inform the patient 104 that help is on the way.

As mentioned above, patient worn sensors included as part of the system 100 can include the wrist sensor 106. The wrist sensor 106 can be used to track and record blood pressure and blood oxygenation (SpO2) for the patient 104. As with the chest sensor 102, the wrist sensor 106 can include both reusable and disposable portions. For example, the wrist sensor 106 can include a reusable housing and circuitry for processing signals received from the patient 104 and a disposable portion for contacting the skin of the patient 104.

In some implementations, the patient worn sensors include a finger sensor 107 that extends from the wrist sensor 106 and engages one or more fingers of the patient 104. The finger sensor 107 can be used, for example, to measure blood oxygenation (SpO2) for the patient 104. In some implementations, rather than being located at the wrist of the patient 104, the wrist sensor 106 can take the form of an upper arm sensor that is located at the upper arm (above the elbow) of the patient 104. The upper arm sensor can be used, for example, to measure blood pressure for the patient 104.

In some implementations, the monitoring devices can include a bedside monitor 108. The chest sensor 102 can communicate with the bedside monitor 108 to convey information collected by the chest sensor 102 and/or other patient worn sensors (e.g., patient vital signs, patient activity, patient location) to the bedside monitor 108. For example, the chest sensor 102 can wirelessly communicate with the bedside monitor 108 using Bluetooth technology. As another example, the chest sensor 102 can communicate with the bedside monitor 108 using a WiFi protocol or a cellular protocol. As yet another example, the chest sensor 102 can use a wired connection to communicate with the bedside monitor 108. The communication connection between the chest sensor 102 and bedside monitor 108 can also be used to relay information from the bedside monitor 108 to the chest sensor 102. For example, the bedside monitor 108 can be used to change settings for the chest sensor 102, such as acceptable ranges for heart rate, respiratory rate, blood oxygenation, or other vital signs monitored by the chest sensor 102 and/or other patient worn sensors. As another example, the bedside monitor 108 can be used to change a frequency at which particular vital signs for the patient 104 are captured and transmitted by the chest sensor 102 and/or wrist sensor 106. As yet another example, the bedside monitor 108 can be used to change a sensitivity level of one or more vital sign reading components of the chest sensor 102 and/or wrist sensor 106.

In some implementations, the wrist sensor 106 also communicates with the bedside monitor 108 (e.g., through a wireless Bluetooth connection, other wireless connection, or through a wired connection). In some implementations, the wrist sensor 106 does not communicate directly with the bedside monitor 108, but rather transfers information to the chest sensor 102 (e.g., through a wireless or wired connection) and the chest sensor 102 then transfers information collected by the wrist sensor 106 to the bedside monitor 108 and transmits settings information and other information indicated by the bedside monitor 108 to the wrist sensor 106.

In some implementations, various different vital signs are recorded at different sampling rates and the buffered and sent to the bedside monitor (and therefore to other computing devices in direct or indirect communication with the bedside monitor) at a unified, consistent rate. For example, raw data for an ECG waveform can be sampled at 200 samples per second, while blood oxygenation and bio-impedance are sampled at 33 samples per second. This various information sampled at different rates can be buffered together such that it is all bushed to the bedside monitor at a consistent rate (e.g., 9 times per second).

The bedside monitor 108 can allow a caregiver 110 (e.g., a nurse, doctor, orderly, physical therapist, or other caregiver) to view real-time vital signs for the patient 104, past vital signs for the patient 104, other information provided by the chest sensor 102, wrist sensor 106, and/or other patient worn sensors, or other information associated with the patient 104. For example, the bedside monitor 108 can display an ECG waveform for the patient 104 while also listing a current blood oxygenation level, blood pressure, hydration level, heart rate, respiration rate, and body temperature for the patient 104. The caregiver 110 can also use the bedside monitor 108 to make notes regarding patient care for the patient 104, make annotations for vital sign information or other patient information, send messages to other caregivers, or log patient activities. For example, the caregiver 110 can use the bedside monitor 108 to make a note that the patient 104 has experienced mild trouble breathing, or that the patient 104 is experiencing limb pain. As another example, the caregiver 110 may be a physical therapist and can use the bedside monitor 108 to log a therapy activity for the patient 104 and make notes about physical therapy progress for the patient 104. As yet another example, the caregiver 110 can use the bedside monitor 108 to adjust ranges for what is considered a "normal" or "safe" range for one or more vital signs for the patient 104. As yet another example, the caregiver 110 may be a hospital orderly and can use the bedside monitor 108 to record when the patient 104 has eaten meals, and how much the patient 104 has eaten at each meal. Although described herein as a bedside monitor, it should be understood that some or all of the display, communication, sensor control, and other functionality of the bedside monitor 108 can be performed by one or more devices that are remote from the chest sensor 102. For example, the bedside monitor 108 can be a computer or tablet device that is located remotely from the patient 104 and chest sensor 102 and communicates through one or more network connections to receive and/or send information from/to the chest sensor 102 using techniques described in greater detail below.

The bedside monitor 108 can also be used to review notes on patient care for the patient 104 left by other caregivers, or track patient vital signs and activity for a period of time in order to assist in diagnosis or prevention of complications. The bedside monitor 108 can also convey information associated with alarm states for the chest sensor 102. For example, if any of the various vital signs or other information (such as patient motion/location) falls outside of specified "safe" limits, the chest sensor 102, wrist sensor 106, or bedside monitor 108 can initiate an alarm state. The bedside monitor 108 can alert the caregiver 110 to the alarm state through use of visual or audio alarms. In some scenarios, different visual or audio alarms can be used for distinct types of alarm states, or for varying emergency levels associated with different alarm states. In some implementations, alarm states can be tiered based on the severity of an alarm state, with some alarms being identified as more important (and/or in need or more immediate attention from a caregiver) than others. For example, if the chest sensor 102 detects cardiac arrest, this can be classified as a high level emergency requiring immediate attention, while if the wrist sensor 106 detects a slightly elevated blood pressure, this can be identified as a low level alarm state that does not need to be addressed until the next time a caregiver checks in with the patient 104. A display of the bedside monitor 108 can indicate various alarm states to the caregiver 110, as well as the relative importance or level of each alarm state. The caregiver 110 can then use the bedside monitor 108 to view additional information associated with each alarm state, including changes in vital signs or other patient associated information that prompted initiation of the alarm state.

In some implementations, the chest sensor 102, wrist sensor 106, and/or other patient worn sensors can include circuitry for processing vital sign information and other information recorded by the sensors to identify when one or more alarm states have occurred. In some implementations, the patient worn sensors transmit raw, pre-processed vital sign information and other information collected in association with the patient 104 to the bedside monitor 108 and the bedside monitor 108 analyzes the raw information to determine various vital signs and other information for the patient 104 and identify if any alarm states are present (e.g., by identifying if any vital signs or other signals have deviated from an acceptable range). In still other implementations, other portions of the system 100 may be used to analyze vital sign and other information collected by the chest sensor 102 and wrist sensor 106 to identify alarm states associated with the patient 104.

In some implementations, an alarm state for the patient 104 can be identified by comparing one or more vital signs collected for the patient 104 to threshold values. For example, the patient 104's heart rate can be compared to a threshold heart rate value, if the patient 104's heart rate falls below the threshold value, one or more components of the system 100 can automatically determine that the patient is experiencing cardiac arrest. The system 100 can then send alerts to one or more caregivers indicating the cardiac arrest alarm state for the patient 104. For example, an alert can be sent to one or more caregivers within a predetermined proximity of the patient 104, a supervising nurse for a hospital ward in which the patient 104 is located, and a general care physician responsible for general care for the patient 104. An alert can also be sent to a cardiologist currently on duty at the healthcare facility where the patient 104 is located.

In some implementations, collected vital signs can be compared to threshold values to not only determine a type of alarm state, but also to identify a severity of an alarm state. For example, a patient experiencing a respiration rate that is slightly above the preferred range for the patient can be identified as having a respiratory alarm state of a tier 2 level while a patient experiencing a respiration rate that deviates significantly from a preferred range can be identified as having a respiratory alarm state of a tier 1 level (e.g., a higher urgency level). As indicated in the preceding example, alarm states can be divided into different tier levels. As another example, information collected by an accelerometer included in the chest sensor 102 can indicate that the patient 104 has fallen. If the distance and velocity of the fall can be compared to threshold values to identify a severity for the fall and associate an alarm state tier level for the fall. For example, a slow fall from a height of two feet can have a severity level of tier 2 while a quick fall from a height of five can be assigned a severity level of tier 1.

In addition to communicating with the chest sensor 102, wrist sensor 106, and/or other patient worn sensors, the bedside monitor 108 can also communicate with one or more service brokers 113 through a network 112. The service broker 113 can collect information provided by various monitoring devices including the bedside monitor 108, other bedside monitors, various sensors, and other computing terminals.

The service broker 113 can comprise multiple servers that are co-located, or multiple servers located at distinct geographic locations to provide so called "cloud" storage for information stored by the system 100. The service broker 113 can be accessed through the network 112 from many different locations by various monitoring devices or client devices. For example, the service broker 113 can be accessed by the bedside monitor 108, other bedside monitors and computing devices located at the same hospital as the bedside monitor 108, and various bedside monitors and other computing devices (e.g., mobile phones, personal computers, tablet devices, etc.) located at other physical locations.

The system 100 further includes a client device 114. For example, the client device 114 can be a central server station, a mobile device, or a laptop. Information collected by the service broker 113 can be accessed at a client device 114. For example, a caregiver 116 or other hospital personnel can use the client device 114 to access information for the patient 104, other patients, or other hospital or healthcare administrative functions. The network 112 can be an intra-hospital local area network (LAN) such as a WiFi network, a wide area network (WAN) such as the Internet, or any combination of LAN and WAN networks. The bedside monitor 108 can connect to the network 112 using a wireless protocol such as WiFi or a cellular communication protocol, or through a wired connection. In some implementations, the client device 114 may be located at a distinct facility from the patient 104 and bedside monitor 108.

The client device 114 can allow the caregiver 116 to monitor vital signs, activities, and other information for the patient 104 from a remote location. The client device 114 can additionally allow the caregiver 116 to observe information for multiple patients within a healthcare facility or system simultaneously. In some implementations, all information collected by the patient worn sensors (e.g., the chest sensor 102 and the wrist sensor 106) and all information entered using the bedside monitor 108 is stored by the service broker 113 and is accessible through the client device 114. In some implementations, the caregiver 116 can receive alarms or alerts associated with the patient 104 at the client device 114 and take appropriate actions to dispatch one or more caregivers to address the alarm situation. In some implementations, the system 100 can automatically recognize an alarm state for the patient 104 and alert an appropriate caregiver to respond to the situation. For example, the bedside monitor 108 can analyze information received from the chest sensor 102 to determine that the patient 104 is choking. The bedside monitor 108 can recognize this as an emergency level alert, and transmit this information to the service broker 113. The service broker 113 can then identify one or more caregivers within close proximity to the patient 104 and alert them that the patient 104 is choking.

The alerts can be sent to the one or more caregivers, for example, through bedside monitors with which the caregivers are currently interacting, computer terminals in communication with the service broker 113, mobile devices carried or worn by the caregivers, or alarms or displays located throughout a hospital or healthcare facility where the patient 104 is located. The service broker 113 can also transmit alert information regarding the patient 104 to the client device 114 to notify the caregiver 116 as well as the beside monitor 108 (which is associated with the chest sensor 102 worn by the patient 104) to alert the caregiver 110 or perhaps one or more other caregivers in the vicinity of the bedside monitor 108. This automated recognition of an alarm state for the patient 104 and routing of the alarm to caregivers within close proximity to the patient 104 can reduce the time taken to respond to and resolve the emergency, thereby reducing adverse effects for the patient 104.

In some implementations, in addition to information collected by the various patient worn sensors (such as the chest sensor 102, wrist sensor 106, and/or other patient worn sensors) the bedside monitor 108 can include functionality for collecting information related to the patient 104. For example, the bedside monitor 108 can include one or more cameras for monitoring movements, posture, and other aspects of the patient 104. The cameras can be built in to the bedside monitor 108, attached to the bedside monitor 108 as peripheral devices, or separate devices in wired or wireless communication with the bedside monitor 108. A camera of the bedside monitor 108 can be positioned to face the patient 104 while the patient 104 is located in the bed and monitor movements of the patient 104. This information can be used to recognize alarm states for the patient. For example, the bedside monitor 108 (or another computing device of the system 100, such as the service broker 113) can analyze video images captured by the camera to identify if the patient 104 has fallen out of the bed. As another example, the camera can be used to identify that the patient 104 is not located in the bed at a time when the patient 104 is expected to be located in the bed. If the bedside monitor 108 detects that the patient 104 has been out of bed for longer than a threshold period of time, the bedside monitor 108 can recognize this as an alarm state and alert a caregiver to the situation.

As yet another example, the camera of the bedside monitor 108 can determine that the patient 104 is awake. Stored information for the patient 104 can indicate that the patient 104 should currently be under a medication induced sleep. The bedside monitor 108 can recognize that the patient 104 being awake during a period when the patient 104 should be asleep as an alarm state. As yet another example, the camera can be used to recognize that a comatose patient is awake and moving. The bedside monitor 108 can recognize this as an alarm state and alert a caregiver to check on the now awake patient.

The bedside monitor 108 can further include one or more accelerometers for determining an orientation of the bedside monitor 108. This orientation information can further be used to determine an orientation of various images captured by the camera of the bedside monitor 108. For example, the bedside monitor 108 may be positioned at various different angles depending on how the bedside monitor 108 is positioned with respect to the patient 104. For example, the bedside monitor 108 may be connected to a support post, affixed to a railing of the patient 104's bed, affixed to the wall, or placed on a table or bedside stand. Additionally the bedside monitor 108 may not necessarily be completely flush on a surface that is supporting the bedside monitor 108. The orientation of the bedside monitor 108 can differ depending on how the bedside monitor 108 is supported. The accelerometers can be used to determine the bedside monitor 108's orientation and thereby determine the orientation of images captured by the camera of the bedside monitor 108.

In some implementations, the chest sensor 102 also includes one or more accelerometers than can determine movements of the chest sensor 102 and orientation of the chest sensor 102.

Other information that can be collected by one or more sensors or devices built into or in communication with the bedside monitor 108 can include environmental temperature, environmental humidity, noise level, light level, carbon monoxide detection, or smoke detection. For example, the bedside monitor 108 can identify that environmental temperature near the patient 104 has fallen below an acceptable level and alert a caregiver or maintenance worker to the change in temperature. As another example, the bedside monitor 108 can detect that environmental humidity has dropped below a threshold value.

In some implementations, caregivers associated with the patient 104 can be classified into different caregiver categories. For example, first tier caregivers can be identified as caregivers who are responsible for the immediate or day to day care of the patient 104, while second tier caregivers can be identified as caregivers responsible for more generalized supervision of the patient 104's recovery or treatment. For example, an attending physician for a ward where the patient 104 is located could be identified as a first tier caregiver for the patient 104 while a speech therapist responsible for meeting with the patient and working on speech skills once per week could be classified as a second tier (or in some cases, even a third tier) caregiver for the patient 104. As another example, an immediate relative of the patient 104 who responsible for care of the patient 104 when the patient is at home can be identified as a third tier caregiver for the patient 104. The same caregiver can have different caregiver classification levels for different patients. For example a physical therapist can be a first tier caregiver for a patient with which the physical therapist meets several times per day for long periods, while the physical therapist can be a second tier caregiver for a patient who only meets with the physical therapist once per week.

In some implementations, when a patient event (such as an alarm state identified based on vital sign information, or another patient event) occurs for the patient 104, different alerts can be sent to different caregivers. In some implementations, the different alerts can be sent to caregivers based on the caregiver classifications for the caregivers. For example, a detailed alert that includes details on a particular alarm state for the patient 104 and instructions on how to respond to the alarm state can be transmitted to an attending physician on duty at a ward where the patient 104 is located (a first tier caregiver) while a less detailed alert that merely indicates the alarm state and a time when the alarm state occurred can be sent to the patient 104's general care family doctor (a second tier caregiver for the patient 104). As another example, components of the system 100 can determine that the patient 104 is choking based on vital sign information collected by the chest sensor 102. The system 100 can send an urgent alert to a nurse located within a close proximity to the patient 104 that indicates that the patient is choking and instructing the nurse to clear the patient 104's airway. A different alert can be sent to the patient 104's identified emergency contact (e.g., parent, spouse, sibling, etc.) that indicates that the patient experienced a choking situation, and perhaps also indicating that the choking situation was addressed and the patient 104 is no longer in danger.

In some implementations, alerts can be generated in response to detection that a patient is in an unexpected location, or that the patient has been in a particular location for longer than a specified period of time. For example, a patient can be located in a recovery room after a surgery. The patient can be scheduled to be moved to a room in a general ward of the hospital within a certain time frame (e.g., under 8 hours). One or more computing devices of the system 100 can identify that the patient has been located in the recovery room for longer than eight hours and generate an alert to provide to one or more caregivers indicating that the patient is still located in the recovery room. As another example, one or more computing devices of the system 100 can determine that the patient was supposed to be discharged from the hospital within a particular time window. If the patient is identified as still being located within the hospital after the specified time window has elapsed, the system 100 can generate an alert and provide the alert to one or more caregivers indicating that the patient was supposed to have been discharged. As yet another example, an alert can be generated and provided to one or more caregivers if a patient is identified as being immobile in a stairwell for more than a specified period of time (e.g., one minute).

In some implementations, alerts regarding situations other than patient associated alarm states can also be sent to caregivers or other users of the system 100. For example, an alert indicating that the bedside monitor 108 has lost communication with the chest sensor 102 can be sent to the caregiver 110. As another example, an alert indicating that a battery of the chest sensor 102 is law can be sent to the caregiver 110. As yet another example, an alert indicating that the chest sensor 102 is not properly collecting information necessary for one or more vital sign determinations for the patient 104 can be transmitted to the caregiver 110. In this example, the caregiver 110 can address the problem by adjusting contacts of the chest sensor 102 so that they properly contact the skin of the patient 104, or by replacing the chest sensor 102 with a properly functioning chest sensor.

In some implementations of the system 100, the chest sensor 102, wrist sensor 106, and/or other patient worn sensors can obviate the need for the bedside monitor 108 by connecting directly to the network 112 (e.g., using a WiFi or other wireless protocol) to transfer vital sign and other information to the service broker 113. The information transferred to the service broker 113 through the network can then be accessed at the client device 114 and other terminals connected to the network 112. In some implementations, the bedside monitor 108 serves as a dummy terminal that receives information from the service broker 113 and displays a graphical user interface dictated by the service broker 113 rather than receiving information directly from the chest sensor 102 and/or other patient worn sensors.

In some implementations, information for the patient 104 (such as vital signs, alarm states, treatment information, biographical information, etc.) can be accessed using other devices in communication with the service broker 113 and/or bedside monitor 108. For example, patient information can be sent to a mobile device (such as a smart phone, tablet or laptop) owned by the caregiver 110 or another caregiver associated with the patient 104. As another example, the caregiver 110 can access the service broker 113 (e.g., by using the bedside monitor 108 or another computing device) and indicate that the caregiver 110 wishes to receive updates for the patient 104. The caregiver 110 can then be associated with the patient 104 (for example, by linking a caregiver profile for the caregiver 110 to a patient profile for the patient 104). When important information regarding the patient 104 (such as alarm states, or significant changes in treatment plans) are received by the service broker 113, the service broker 113 can automatically send this information to a device associated with the caregiver 110, such as the caregiver 110's mobile phone.

In some implementations, a caregiver associated with the patient 104 can use a computing device to communicate with the service broker 113 and access information for the patient 104. For example, a caregiver can access information for the patient 104 if the caregiver has proper permission to access the information. The caregiver can indicate permission to access the information by entering an access code, or by accessing a profile for the caregiver that has previously been associated with a patient profile for the patient 104. In some implementations, information associated with the patient 104 can be accessed from a number of different bedside monitors or client devices. Such an information access scheme can allow caregivers and other users of the system 100 to access information for multiple patients. For example, a doctor can be in charge of monitoring the status of a number of patients. The doctor can use a PC to access the service broker 113 and view vital sign information, alert information, and other information for each of the multiple patients. The information for the multiple patients can be arranged in a newsfeed that allows the doctor to easily access and review the most pertinent patient information, while also providing the ability for the doctor to access additional information for each patient that is not identified by the system 100 as being the most relevant.

The caregiver 110 can additionally use the bedside monitor 108 to access information associated with the patient 104 that has been entered into the system 100 but not provided by the chest sensor 102 or other patient worn sensors. For example, the caregiver 110 can use the bedside monitor 108 to access information associated with the patient 104 regarding treatment or procedures that occurred at locations other than the current location of the patient 104. In one example, the caregiver 110 can use the bedside monitor 108 to access and review information stored at the service broker 113 regarding interactions between the patient 104 and emergency room staff to assess a current status for the patient 104. As another example, the caregiver 110 can review notes left by an anesthesiologist at a different bedside monitor for the patient 104 regarding specific vital signs or other behavior for the patient 104 to observe during a specified post-surgical procedure time period for the patient 104.

In some implementations, the service broker 113 can interface with computing systems outside of the system 100 to access additional information for the patient 104. For example, the service broker 113 can access electronic medical records (EMRs), electronic health records (EHRs), or picture archiving and communication system (PACS) information for the patient 104 containing healthcare information for the patient regarding past treatment, procedures, care plans, diagnoses or other healthcare related information for the patient 104 which may or may not be associated with a healthcare facility associated with the system 100.

As discussed above, the various components of the system 100 can allow caregivers (including the caregivers 110 and 116) to more efficiently coordinate patient care and more seamlessly transition a patient from one location to another, from one environment to another, or from one set of caregivers to another. For example, caregivers can use the system 100 to make notes regarding patient care which can be stored along with patient vital sign and other information. For example, the caregiver 110 can make a note about the patient 104's eating habits. As another example, the caregiver 116 can use the client device 114 to enter notes for the patient 104 that are, for example, based on reviewing and assessing information received from the bedside monitor 108 and other sources and stored at the service broker 113. The notes can then be viewed by other caregivers when the caregivers access information about the patient 104 (e.g., using the client device 114, the bedside monitor 108, another bedside monitor, a mobile device, or another computing device in communication with the network 112) to allow the other caregivers to adjust one or more aspects of the patient 104's treatment plan. In some implementations, a note or message can be addressed to the attention of one or more other caregivers. For example, a the caregiver 110 can make a note that the patient 104 had a particular reaction after taking medication and set the note to the attention of a pharmacist responsible for care of the patient. The pharmacist can receive an alert (e.g., via the pharmacist's mobile phone) that a new note has been addressed to his attention, review the note, and review other information associated with the patient 104 to best determine if a change to the patient 104's medication schedule needs to be made.

In some implementations, the service broker 113 can include information other than information directly related to patient care. For example, the service broker 113 can store information related to healthcare facility maintenance and inventory (e.g., for medical supplies, medical devices, medication, or routine items such as light bulbs and batteries). This information can be accessed from computing devices included in the system 100 that are in communication with the network 112. The system can further include functionality for tracking maintenance and inventory, including scheduling maintenance, tracking maintenance progress, ordering new inventory as supplies are depleted, tracking supplier, vendor, and service provider information, and tracking maintenance and inventory budgets. The service broker 113 can also store insurance information for patients, payment information for patients, or other patient information that is only tangentially related to patient care. Additional functionality that can be provided by the service broker 113 or other components of the system 100 includes employ payroll and staff scheduling.

In some implementations of the system 100, multiple patient worn sensors are associated with multiple respective patients and each of the patient worn sensors is configured to sync with one or more bedside monitors or intermediary devices (e.g., using Bluetooth or another wireless communication protocol). In some implementations, the patient worn sensors can communicate with bedside monitors or other devices using wired connections. In some implementations, some or all of the patient worn sensors are configured to communicate directly with the network 112 (e.g., using WiFI or another wireless communication protocol). Information collected by the multiple patient worn sensors can be routed through the network to the service broker 113 and stored. The information can then be accessed by components of the system 100. For example, the caregiver 116 can access information collected by the multiple patient worn sensors at the client device 114 to monitor statuses of the patients associated with the multiple patient worn sensors.

In some implementations, multiple bedside monitors included in the system 100 can communicate directly with each other to create network redundancy. For example, the network 112 may be down for a period of time, or the bedside monitor 108 and other bedside monitors of the system 100 may be unable to communicate with the network 112 for a period of time. The bedside monitor 108 may communicate with the service broker 113 and other computing devices of the system 100, for example, through a LAN. The LAN may experience an outage and be unavailable for a period of time. The bedside monitors of the system 100 can detect the outage and each bedside monitor can establish direct communications with one or more other bedside monitors (or other computing devices of the system 100) to form an ad hoc backup network for conveying patient information and other information among bedside monitors and other computing devices of the system 100. For example, each of the bedside monitors can use wireless communication capabilities (e.g., Bluetooth or WiFi communication capabilities) to communicate with other bedside monitors within range.

In many use cases, the bedside monitors will be positioned somewhat regularly throughout a hospital or other medical care environment. For example, there would generally be one or two bedside monitors located in each patient room as well as computing devices of the system 100 having wireless communication capabilities positioned at nursing stations and other area throughout the hospital. The spatial distribution of the bedside monitors can allow the bedside monitors to relay information through a series of bedside monitors (and other computing devices) to allow information to be transmitted to be transmitted between devices that are physically further apart from each other than could normally be spanned by standard short range wireless communication protocols.

In use, one or more patient worn sensors (such as the chest sensor 102 and wrist sensor 106) can be associated with the patient 104 upon admittance of the patient 104 to a healthcare facility, or shortly after admittance of the patient 104 to the healthcare facility. In some implementations, if the patient 104 has entered the healthcare facility during an emergency situation (e.g., cardiac arrest, severe car accident, etc.) the patient worn sensors can be issued to the patient 104 after the emergency situation has been addressed and the patient 104 has been stabilized. In some implementations, the patient 104 can be associated with a unique patient identifier ("ID"). The patient ID can be as simple as the patient 104's name, a unique number assigned to the patient 104, a unique combination of numbers, letters, and other characters, or any other unique identifier associated with the patient 104. If the patient 104 has previously interacted with the healthcare facility, the system 100, or a related system, the caregiver 110 can look up the unique identifier for the patient 104 by, for example, entering the patient 104's name at the bedside monitor 108. The caregiver 110 can then access patient information for the patient 104. Patient information can include biographical information such as name, age, weight, height, address, contact information, family members, emergency contacts, etc. as well as healthcare information regarding past (or present or future) healthcare events, treatments, procedures, care plans, etc. for the patient 104. In some implementations, the caregiver 110 can access a patient profile for the patient 104 (for example, using the patient ID for the patient 104). The patient profile can include any of the above listed information for the patient 104. The patient profile can also indicate caregivers associated with the patient 104, such as doctors who have performed surgery on the patient 104, doctors scheduled to perform future procedures on the patient 104, one or more caregivers responsible for the primary care of the patient 104, emergency room doctors and attendants who handled initial emergency care for the patient 104, and other caregivers associated with the patient 104.

If the patient 104 has not previously interacted with system 100 or a related system, a new unique ID can be assigned to the patient 104 by one or more components of the system 100 (for example, by the bedside monitor 108 or the service broker 113.) Biographical, healthcare, and other information for the patient 104 can then be entered (e.g., using the bedside monitor 108 or client device 114) and stored at the service broker 113.

When the patient worn monitors (such as the chest sensor 102 and wrist sensor 106) are initially provided to the patient 104, the patient worn sensors can be associated with the patient 104 by associating the patient worn sensors with the unique ID for the patient 104. For example, the chest sensor 102 can be synced with the bedside monitor 108. The caregiver 110 can then use the bedside monitor 108 to associate the chest sensor 102 with the patient 104. After the chest sensor 102 is associated with the patient 104, the chest sensor 102 can identify the patient 104 to other components of the system 100, such as other bedside monitors, or other monitor stations.

The bedside monitor 108 can sync with the chest sensor 102, for example, by searching for devices within a specified distance of the bedside monitor 108, displaying a list of nearby devices (such as the chest sensor 102, the wrist sensor 106, and one or more other patient worn sensors worn by other nearby patients), and allowing the caregiver 110 to select the chest sensor 102 from the list of displayed devices. After syncing, the caregiver 110 can associate the chest sensor 102 with the patient 104's unique patient ID. As another example, the caregiver 110 can sync the bedside monitor 108 with the chest sensor 102 by entering a unique sensor ID for the chest sensor 102 at the bedside monitor 108. The unique sensor ID can be, for example, printed on the surface of the chest sensor 102. In some implementations, the bedside monitor 108 is synced with the chest sensor 102 using a special scanning device in communication with the bedside monitor 108. The caregiver 110 can use the scanning device to scan the chest sensor 102 (e.g., by detecting a signal being transmitted by a component of the chest sensor 102, scanning an RF ID tag, or by reading a barcode printed on the chest sensor 102). The bedside monitor 108 can use information from the scanning device to identify the chest sensor 102 and sync with the chest sensor 102. In some implementations, the bedside monitor 108 can include a scanning device that is incorporated into the design of the bedside monitor 108. For example, the bedside monitor can be a tablet device that has one or more built in cameras that can be used to scan the chest sensor 102.

In some implementations, the bedside monitor 108 can automatically sync patient worn sensors or other devices with which the bedside monitor 108 has previously synced whenever the patient worn sensors and other devices are within a communication range of the bedside monitor 108. For example, the chest sensor 102 can be synced with the bedside monitor 108 using one of the above described techniques, or another technique. The patient 104 can then leave a communication range of the bedside monitor 108, for example by going to a hospital cafeteria to eat lunch or going to a physical therapy area of the healthcare facility. The patient 104 can then return to the communication range of the bedside monitor 108. The bedside monitor 108 can automatically detect that the chest sensor 102 has reentered the communication range of the bedside monitor 108, that the bedside monitor 108 and chest sensor 102 had previously been synced, and then sync with the chest sensor 102. In some implementations, the bedside monitor 108 automatically syncs with all patient worn sensors within a specified communication range that are capable of communicating with the bedside monitor 108. For example, the bedside monitor 108 can sync with patient worn sensors for multiple patients located in the same room and display information received from each of the sensors.

In some implementations, patient worn sensors can sync with any monitor (such as a bedside monitor) within a specified communication distance. In some implementations, a patient worn sensor can identify a nearest monitor from among several monitors (e.g., by strength of communication signal) and automatically sync with the identified nearest monitor. In some implementations patient worn sensors are capable of syncing with multiple monitors simultaneously. In some implementations, syncing activity of a patient worn sensor can be used to track movements of a patient. For example, each monitor can be associated with a particular physical location. In this example, the bedside monitor 108 might be associated with room 309 of the healthcare facility. In some implementations, when monitors are moved, they become associated with a new physical location. Continuing with this example, the patient 104 can leave a room in which the bedside monitor 108 is located (i.e., room 309).

Figure 2:
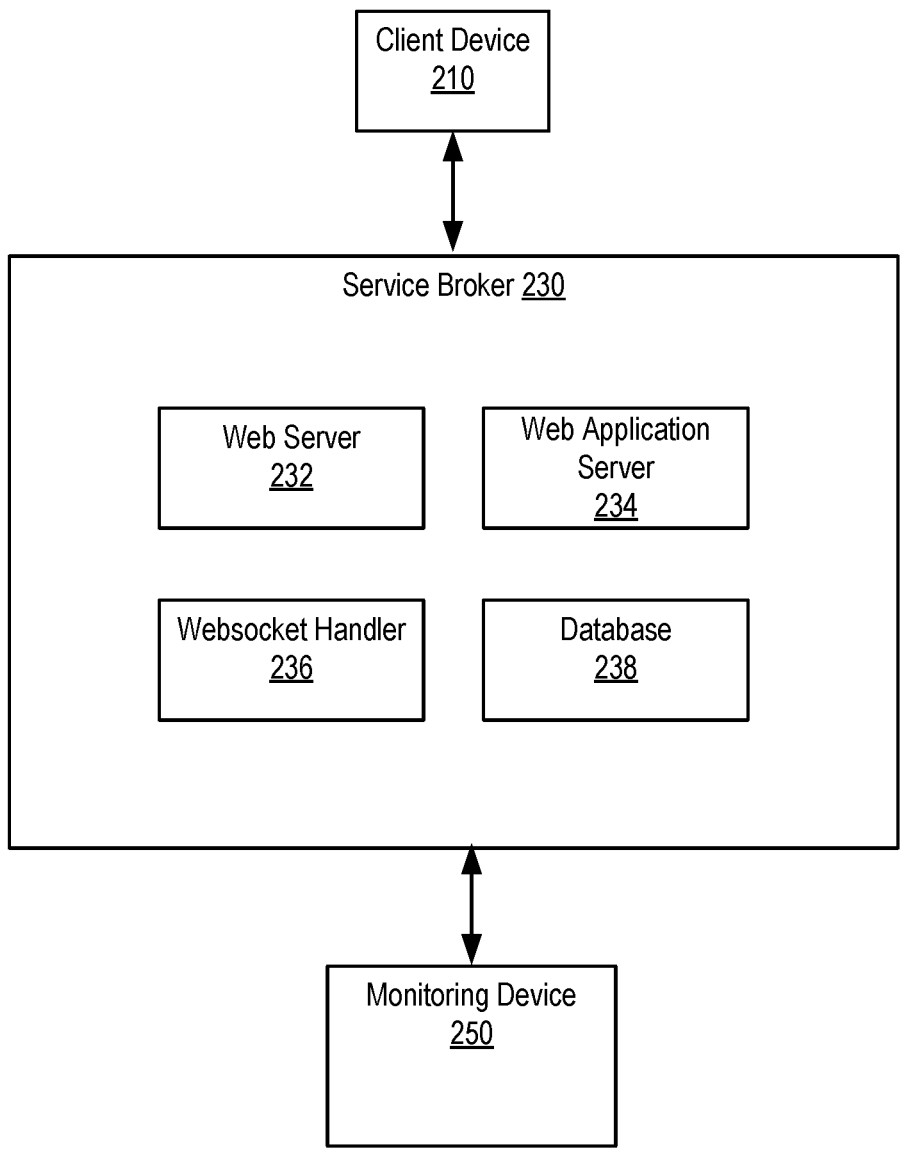
FIG. 2 is a diagram illustrating an example system to monitor a waveform obtained from a patient and provide realtime medical data to a client device.

FIG. 2 is a diagram illustrating an example system 200 to monitor a waveform and/or other realtime information obtained from or in association with a patient. The system 200 is implemented on one or more computers. In some implementations, the system 200 can be, or include components of, the system 100 in FIG. 1. The system 200 includes a client device 210, a service broker 230, and one or more monitoring devices 250. In some implementations, the client device 210 can be the client device 114 in FIG. 1, the service broker 230 can be the service broker 113 in FIG. 1, and the monitoring devices 250 can be the monitoring devices 102, 106, 107, and 108 in FIG. 1. The service broker 230 includes a web server 232, a web application server 234, a websocket handler 236, and a database 238.

The client device 210 provides a request for a web page to the service broker 230. In some implementations, the request includes patient information for a particular patient. For example, the patient information can include information to identify a particular patient such as a patient's name, a date of birth, a social security number, and a physical address. In some implementations, the request can include a patient identifier for the patient (e.g., a unique ID number). In some implementations, the request can include patient information for multiple patients.

The service broker 230 receives a request for a web page from the client device 210. In particular, the web server 232 of the service broker 230 receives the request for a web page from the client device 210. In some implementations, the service broker 230 can receive the request through an HTTP connection. However, a type of connection between the client device 210 and the service broker 230 is not limited to an HTTP connection. Any suitable type of connection can be established between the client device 210 and the service broker 230 for various implementations. In response to the request, the service broker 230 determines a web page based on patient information included in the request, and provides the web page to the client device through the HTTP connection. The processes for determining a web page and providing the web page will be described in greater detail below with reference to FIG. 3.

The service broker 230 can be an on-demand service broker processing or handling realtime medical data. In some implementations, the service broker 230 obtains realtime medical data from the monitoring device 250 that monitors a patient and obtain realtime medical data from a patient. The service broker 230 allows the client device 210 to access realtime medical data that are generated by the service broker 230 based on raw waveform data obtained from the monitoring device 250. In some implementations, the service broker 230 can be implemented as one or more computers configured as HTTP servers to establish an HTTP connection between the service broker 230 and the client device 210. In some implementations, the service broker 230 can be implemented on a cloud computing platform. The cloud computing platform provides endpoints for a client device, e.g., the client device 210. The cloud computing platform also maintains or stores a database, e.g., the database 238, of realtime medical data. The client device, e.g., a client device 210, can access the service broker 230 using the cloud computing platform.

Responsive to the request for a web page, the web server 232 assigns the request to the web application server 236. The web application server 236 determines a particular web page based on patient information for a particular patient. In some implementations, the web page includes an interface to present data identifying the particular patient corresponding to the patient information included in the request. In some implementations, the interface can be a command line interface (CLI), a graphical user interface (GUI), or various combinations of the two. The web application server 236 provides the web page including the interface to the client device 210. The interface included in the web page will be described in greater detail with reference to FIGS. 6A and 6B. In some implementations, the web page can be provided from the service broker 230 to the client device 210 through an HTTP connection. However, a type of connection between the client device 210 and the service broker 230 is not limited to an HTTP connection. Any suitable type of connection can be used between the client device 210 and the service broker 230 for various implementations.

Upon receiving the web page from the service broker 230, a websocket connection is established between the client device 210 and the service broker 230. In some implementations, when the requested web page is loaded by a web browser of the client device 210, the web page invokes a websocket connection between the client device 210 and the service broker 230. In this example, the web page can include particular commands, e.g., commands programmed in JavaScript, such that the commands can invoke a websocket connection between the client device 210 and the service broker 230.

In particular, to establish the websocket connection between the client device 210 and the service broker 230, the client device 210 provides a websocket connection request to the service broker 230. For example, the websocket connection request can be invoked in response to loading the web page on the client device. In this example, the websocket handler 236 of the service broker 230 receives the websocket connection request. In response to receiving the websocket connection request, the websocket handler 236 of the service broker 230 provides a websocket connection response to the client device 210 to establish a websocket connection between the service broker 230 and the client device 210. When the client device 210 receives the websocket connection response, the websocket connection is established between the client device 210 and the service broker 230.

Once the websocket connection is established, the client device 210 provides a request for realtime medical data to the service broker 230 through the websocket connection established between the client device 210 and the service broker 230. In some implementations, the client device 210 can request realtime medical data for the particular patient identified in the patient information described above. In some implementations, the request for realtime medical data can identify a medical data protocol that defines one or more attributes for the realtime medical data.

In some implementations, the attributes include at least one of an identification, a sampling rate, a plot time, or buffer information. For example, the identification can represent an identification of realtime medical data for a particular patient. The sampling rate can represent a sampling rate to sample raw waveform data that are obtained from the monitoring device 250. The plot time can represent a time period to write raw waveform data to a buffer. The buffer information can represent which buffer will be used to be filled with raw waveform data.

Responsive to the request for realtime medical data, the service broker 230 obtains a set of realtime medical data samples. In some implementations, the set of realtime medical data samples include respective values of attributes for the requested realtime medical data. For example, where the client device 210 provides a request for realtime medical data associated with a particular patient, the websocket handler 238 of the service broker 230 obtains, from one or more databases including the database 238, the set of realtime medical data samples. In this example, the set of realtime medical data samples can include respective values of attributes for the requested realtime medical data. That is, the set of realtime medical data samples can include values of an identification, a sampling rate, a plot time, and buffer information for the requested realtime medical data. In some implementations, the service broker 230 obtains a set of realtime medical data samples directly from one more monitoring devices. For example, with reference to FIG. 1, the service broker 230 can obtain a set of realtime medical data samples from patient worn sensors such as the chest sensor 104, the wrist sensor 106, and the finger sensor 107.

Based on the obtained set of realtime medical data samples, the service broker 230 generates realtime medical data for the particular patient. For example, based on the respective values of attributes for the requested realtime medical data, the service broker 230 generates the realtime medical data for the particular patient. In particular, where the attributes include an identification, a sampling rate, a plot time, and buffer information, the service broker 230 can determine a particular waveform, from raw waveform data that are obtained from one or more monitoring devices, based on the value of the identification. Based on the buffer information, the service broker 230 can determine which buffer will be used to be filled with raw waveform data. Based on the sampling rate, the service broker 230 can determine a sampling rate of the particular waveform. Based on the plot time, the service broker can determine how long the service broker 230 writes the particular waveform in the particular buffer.

Once the service broker 230 writes the particular waveform in the buffer based on the sampling rate for the plot time, the service broker 230 generates realtime medical data based on the waveform data written in the buffer. The service broker 230 provides the generated realtime medical data to the client device 210 through the websocket connection. In some implementations, the service broker 230 stores the generated realtime medical data in the database 238.

The client device 210 receives the realtime medical data from the service broker 230 and provides the realtime medical data to a user of the client device 210. For example, the client device 210 can provide the realtime medical data to a user, e.g., a caregiver or other hospital personnel through an interface. The interface can be a CLI, a GUI, or various combinations of the two. Examples of the interface will be described in greater detail with reference to FIGS. 7A and 7B.

Figure 3:
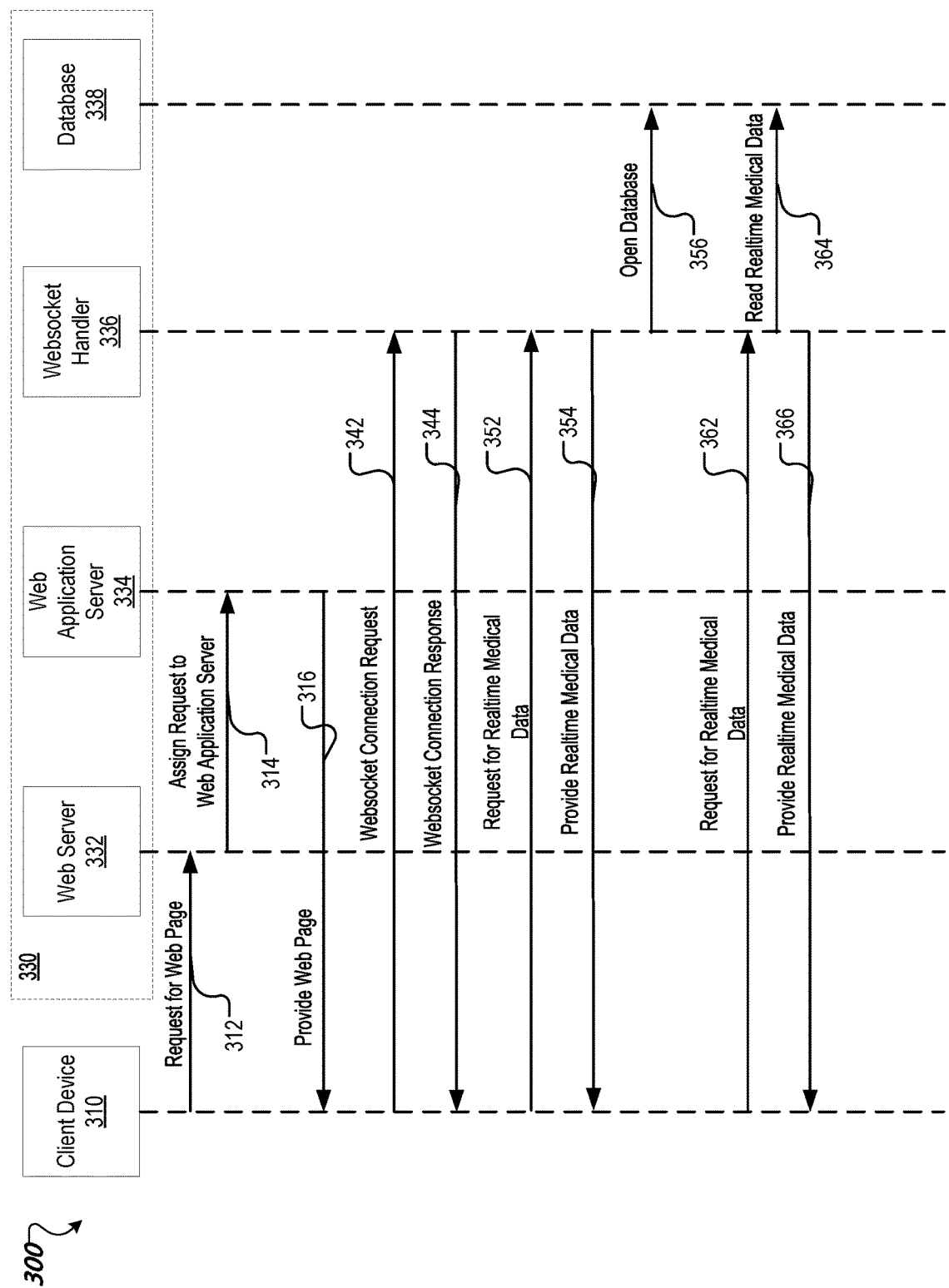
FIG. 3 is a sequence diagram illustrating example operations of providing real time medical data to a client device.

FIG. 3 is a sequence diagram illustrating example operations of providing real time medical data to a client device. In some implementations, a client device 310, a web server 332, a web application server 334, a websocket handler 336, and a database 338 in FIG. 3 can be the client device 210, the web server 232, the web application server 234, the websocket handler 236, and the database 238 in FIG. 2, respectively. In FIG. 3, the system 300 includes the client device 310 and the service broker 330, and the service broker 330 includes the web server 332, the web application server 334, and the websocket handler 336, and the database 338.

The client device 310 provides a request for a web page to the web server 332 of the service broker 330 (Step 312). In some implementations, the request includes patient information for a particular patient. For example, the patient information can include information to identify a particular patient such as a patient's name, a date of birth, a social security number, and a physical address. In some implementations, the patient information can include a unique identifier for the patient, such as a patient ID number or patient ID code. In some implementations, the request can include patient information for multiple patients. In some implementations, the request can be provided through an HTTP connection.

Once the web server 332 receives the request for a web page from the client device 310, the web server 332 assigns the request to the web application server 334 (Step 314). In some implementations, the web server 332 assigns the request to a particular web application server that is dedicated to or associated with a particular patient. For example, each web application server can be assigned to a particular set of patient IDs. For example, where the web application server 334 is dedicated to or associated with the particular patient described above, the service broker 330 can assign the request to the web application server 334.

The web application server 334 determines a web page based on the patient information included in the request, and provide the web page to the client device through the HTTP connection (Step 316). The web application server 334 determines a particular web page based on patient information for a particular patient. For example, the web application server 334 determines a web page identifying data including at least one of a patient's photo, a patient's name, patient's medical data, or patient's personal information. In some implementations, the web page includes an interface to present the data. In some implementations, the interface can be a CLI, a GUI, or various combinations of the two. The web application server 336 provides the web page including the interface to the client device 310. In some implementations, the web page can be provided from the service broker 330 to the client device 310 through an HTTP connection.

Upon receiving the web page from the service broker 330, the client device 310 provides a websocket connection request to the websocket handler 336 to establish a connection between the client device 310 and the service broker 330 (Step 342). For example, when the requested web page is loaded by a web browser of the client device 310, a websocket connection is established between the client device 310 and the service broker 330. In this example, the web page can include particular commands, e.g., commands programmed in JavaScript, such that the commands can invoke the client device 310 to provide the websocket connection request to the websocket handler 330 in response to loading the web page including the commands on the client device 310.

Responsive to receiving the websocket connection request, the websocket handler 336 provides a websocket connection response to the client device 310 (Step 344). When the client device 310 receives the websocket connection response, the websocket connection is established between the client device 310 and the service broker 330.

Once the websocket connection is established, the client device 310 provides a request for realtime medical data to the service broker 330 through the websocket connection established between the client device 310 and the service broker 330 (Step 352). In some implementations, the client device 310 can request realtime medical data for a particular patient. The websocket handler 336 generates realtime medical data as described above with reference to FIG. 2. The websocket handler 336 provides the generated realtime medical data to the client device 310 (Step 354).

The websocket handler 336 accesses the database and opens the database 338 (Step 356). After the websocket handler 336 begins providing realtime medical data to the client device 310, the websocket handler 336 opens the database 338 such that realtime medical data can be provided to the client device 310 without establishing further connections between the client device 310 and the service broker 330. Thus, when the client device 310 provides a subsequent request for realtime medical data (Step 362), the service broker 330 does not need to establish a further websocket connection between the client device 310 and the service broker 330 because the realtime medical data can be provided to the client device 310 through the existing websocket connection established by Steps 342 and 344. This technology improves the network efficiency because it uses less network resources compared to a conventional system that establishes a websocket connection whenever requesting realtime medical data to a service broker.

In response to the subsequent request from the client device 310, the websocket handler 336 reads values of attributes for realtime medical data from the database 338 (Step 364). The websocket handler 336 generates realtime medical data based on the values of attributes read from the database 338. The websocket handler 336 provides the generated realtime medical data to the client device 310 (Step 366).

In some implementations, one or more monitoring device pushes monitored raw waveform data to the service broker 330 asynchronously. In these implementations, the service broker 330 stores the raw waveform data in the database 338. Then, when the service broker 330 receives a request from the client device, the service broker 330 reads appropriate waveform data from the database 338 to generate realtime medical data.

Figure 4:
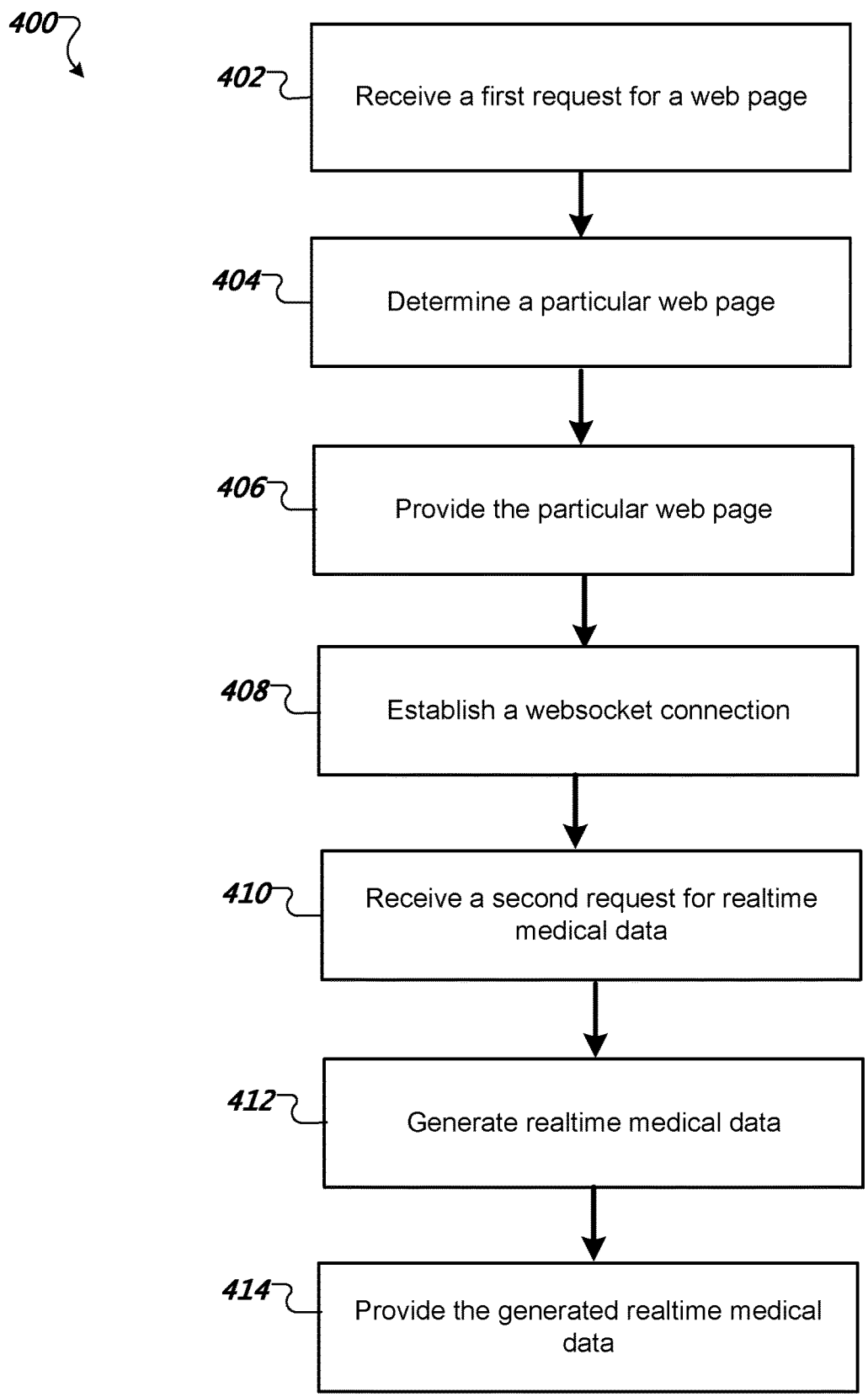
FIG. 4 is a flowchart illustrating an example operations of providing real time medical data to a client device.

FIG. 4 is a flowchart illustrating an example method 400 of providing real time medical data to a client device. For convenience, the method 400 will be described as being performed by a system including one or more computers located in one or more locations. For example, a system, e.g., the system 200 of FIG. 2, appropriately programmed in accordance with this specification, can perform the method 400.

The client device provides a request for a web page to the system (Step 402). In some implementations, the request includes patient information for a particular patient. For example, the patient information can include information to identify a particular patient such as a patient's name, a date of birth, a social security number, and/or a physical address. As another example, the patient information can include a unique patient identifier. In some implementations, the request can include patient information for multiple patients. In some implementations, the request can be provided through an HTTP connection.

Once the system receives the request for a web page from the client device, the system determines a particular web page based on the patient information included in the request (Step 404). For example, the system determines a web page identifying data including at least one of a patient's photo, a patient's name, patient's medical data, or patient's personal information. In some implementations, the web page includes an interface to present the data. In some implementations, the interface can be a CLI, a GUI, or various combinations of the two.

The system provides the web page including the interface to present the data to the client device (Step 406). In some implementations, the web page can be provided from the system to the client device through an HTTP connection.

Upon receiving the web page from the system, the system establishes a websocket connection between the system and the client device (Step 408). For example, when the requested web page is loaded by a web browser of the client device, the client device provides a websocket connection request to the system and the system provides a websocket connection response to the client device such that a websocket connection is established between the client device and the system. In this example, the web page can include particular commands, e.g., commands programmed in JavaScript. The commands can invoke the client device to provide the websocket connection request to the system in response to loading the web page including the commands on the client device.

Once the websocket connection is established, the client device provides a request for realtime medical data to the system through the websocket connection established between the client device and the system 330 (Step 410). In some implementations, the client device can request realtime medical data for the particular patient identified in the patient information described above. The request for realtime medical data can include a request for one or more of heart rhythm (via ECG), heart rate, blood pressure, body temperature, respiratory rate, blood oxygenation, blood glucose level, patient orientation, patient movement, patient sleep state, hydration level, and/or perspiration level. In some implementations, the request for realtime medical data does not indicate types of realtime medical data requested, but rather the system 330 can provide a pre-specified or standard set of data or the system 330 can provide all realtime medical data that is currently available.

The present system allows for a publisher/subscriber relationship. For example, a loosely coupled publish/subscribe pattern is used for the communication between various sub-systems. The system components which send data (e.g., computing devices in communication with patient worn sensors or other patient sensors) will publish messages including realtime data to the broker system (e.g., system 330) on a specific topic. The system components which want to receive data associated with a specific topic (e.g., computing devices being used by one or more caregivers), subscribe to a specific topic channel. At the core of the communication architecture is the broker that aggregates, and routes messages published to specific topics to subscribers of those topics. Topics can include, for example, realtime (time sensitive) telemetry data such as waveform data, vitals, alarms, sensor functionality information, etc.

For example, the system 330 can publish a plurality of channels, each channel containing information on different patients and/or different sets of information for one or more patients. Client devices, such as the client device 310, can subscribe to one or more channels published by the system 330 to receive specific information. For example, for a particular patient, the system 330 can publish multiple channels, with each channel containing different sets of information about the patient and/or one or more medical devices associated with the patient. For example, one channel may include only ECG waveform and heartrate information for the patient. Another channel may include numerous vital signs for the patient including ECG waveform and heartrate information along with a current blood oxygenation level, blood pressure, hydration level, heart rate, respiration rate, and body temperature for the patient. Another channel may include only blood glucose level information for a patient. As yet another example, the system 330 can publish a channel that includes only operational information for a chest sensor and/or one or more other sensors or medical devices associated with the patient, such as a battery level, network connectivity status, or information on the functionality of the sensor/medical device (e.g., information that would be of interest to an IT worker or hospital technician). In this example, interested parties (such as an IT worker) may subscribe to a channel published by the system 330 that includes operational information for all patients within a specific classification, such as all patients in a particular healthcare facility, all patients located in a specific city or region, or all patients currently outfitted with patient worn sensors. Different interested parties can subscribe to different channels published by the system 330 using login credentials. In some implementations, the system 330 will check the login credentials for a particular user logged into a client device (such as the client device 310) to determine if the user is permitted to access a particular channel. If the user is permitted to access the requested channel, the system 330 can provide the relevant information for the patient through the requested channel. In some implementations, different client devices can provide requests for different types of realtime medical data either in the form of subscribing to a specific channel having a particular set of desired medical data for one or more patients or by sending specific requests for types of information to the system 330. In particular, different client devices can request particular types of realtime medical data that are obtained from different monitoring devices. For example, if a client device is a nursing station, the nursing station can request all the realtime medical data that are obtained from different monitoring devices. For example, the client device can identify that all information collected by one or more patient worn sensors should be displayed at the nursing station. As another example, the nursing station can request access to a published channel that includes all information collected by patient worn sensors for a specified collection of patients, such as all patients within a specified ward or on a specified floor of a hospital.

As another example, if a client device is a nursing station desktop, the nursing station desktop can request particular types of realtime medical data that are obtained from particular monitoring devices. In this example, the nursing station desktop can request only realtime medical data that are critical in nature, e.g., heart rate, blood pressure, body temperature, respiratory rate, blood oxygenation, or specific alarms from corresponding monitoring devices. For example, one or more nurses monitoring the nursing station may only be interested in information that indicates a patient status that needs to be addressed immediately. As another example, if a client device is a laptop operated by an IT personnel, the laptop can request realtime medical data such as battery life information from all the monitoring devices that are operated by batteries. In this example, the laptop does not need realtime medical data such as heart rate, blood pressure, body temperature, respiratory rate, and blood oxygenation. Indeed, in this example, the IT personnel may not have permission to access such patient data for data security purposes. As another example, if a client device is a mobile device of a family member of a patient, the mobile device can request a specific sub-set of realtime medical data such as patient orientation information. In this example, the mobile device may not request realtime medical data such as battery life information for monitoring devices operated by batteries. By using websocket connections established between the client device and the service broker, the client device can obtain the requested realtime medical data easily because the service broker can push the realtime medical data to the client device asynchronously.

The system generates realtime medical data (Step 412) and provides the generated realtime medical data to the client device (Step 414) This realtime medical data provided via the websocket connection is displayed concurrently with the surrounding webpage information (e.g., including information about the patient) that had previously been provided via the HTTP connection. The process of generating realtime medical data will be described in greater detail with reference to FIG. 5.

Figure 5:
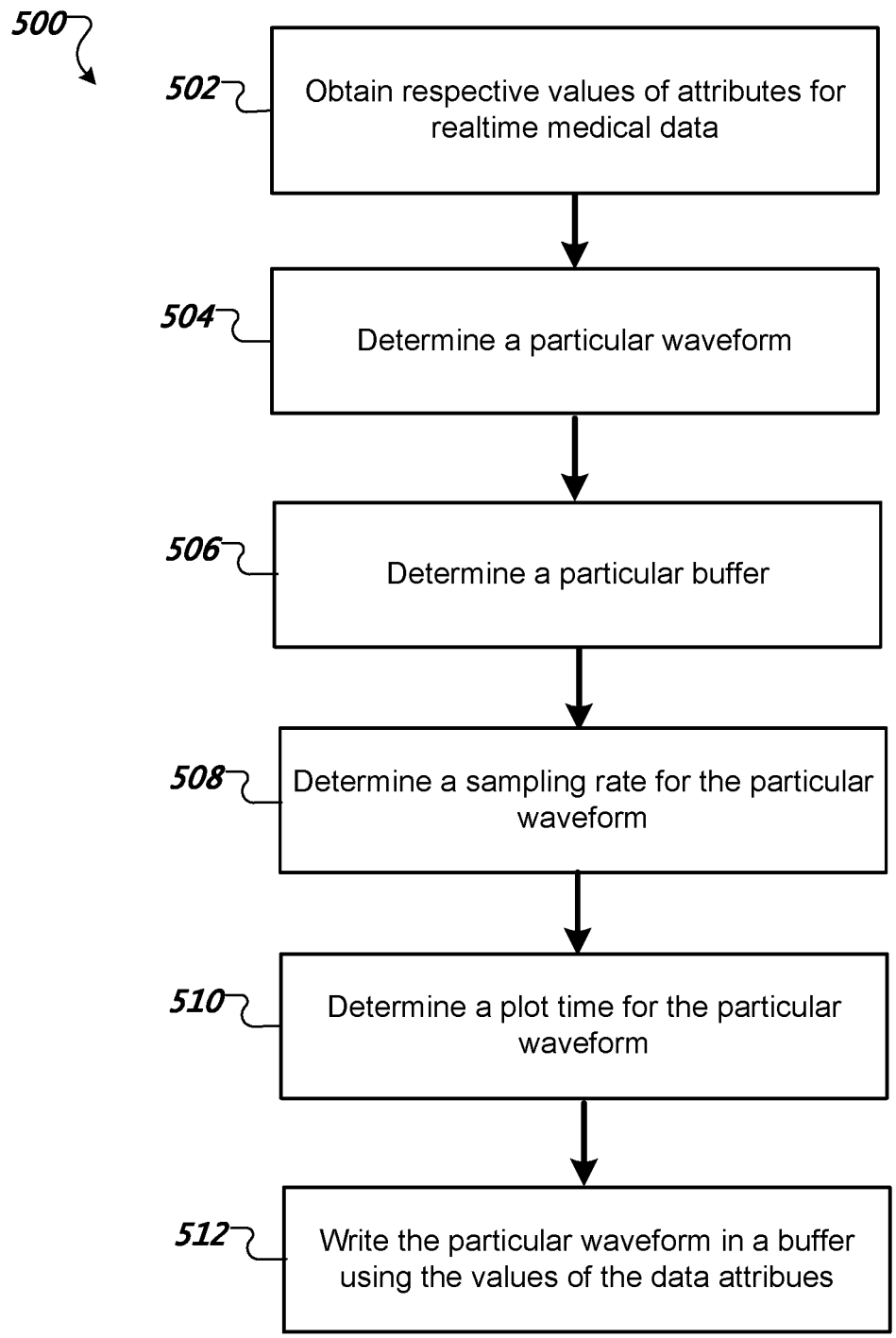
FIG. 5 is a flowchart illustrating an example operations of generating real time medical data.

FIG. 5 is a flowchart illustrating an example method 500 of generating real time medical data. For convenience, the method 500 will be described as being performed by a system including one or more computers located in one or more locations. For example, a system, e.g., the system 200 of FIG. 2, appropriately programmed in accordance with this specification, can perform the method 500.

Where a client device provides a request for realtime medical data to the system through a websocket connection established between the client device and the system, the request for realtime medical data can identify a medical data protocol that defines one or more data attributes for the realtime medical data. In some implementations, the data attributes include at least one of an identification, a sampling rate, a plot time, and buffer information.

To generate realtime medical data, the system obtains values of attributes for the requested realtime medical data (Step 502). For example, when the client device provides a request for realtime medical data associated with a particular patient, the system obtains respective values of attributes for the requested realtime medical data from one or more databases. That is, the system obtains respective values of an identification, a sampling rate, a plot time, and buffer information for the requested realtime medical data. In this example, the realtime medical data include waveform data and the attributes include an identification, a sampling rate, a plot time, and buffer information.

The system determines a particular waveform from one or more waveforms that are monitored by one or more monitoring devices (Step 504). For example, where raw waveform data for multiple waveforms are stored in a database and each waveform is associated with a respective identification for a particular patient, the system can determine a particular waveform based on the value of the identification.

The system determines a particular buffer that will be used to be filled with waveform data (Step 506). For example, based on the buffer information, the system can determine which buffer will be used to be filled with waveform data that are obtained from the database. In some implementations, double buffering techniques can be used to render the waveform data. For example, the client device can include two buffers, i.e., a first buffer and a second buffer. The first buffer can be used to be filled with waveform data. While the first buffer is filled with waveform data, the waveform data stored in the second buffer can be rendered. Upon the first buffer being filled with waveform data (e.g., to a pre-specified level), the function of the two buffers is reversed such that information from the first buffer is rendered while the second buffer receives waveform data. Thus, by using the two buffers, the client device can process the waveform data in realtime efficiently.

The system determines a sampling rate of the particular waveform (Step 508). For example, based on the value of the sampling rate, the system can determine the sampling rate at which the realtime medical data will be sampled based on raw waveform data stored in the database. In some implementations, different sampling rates can be used for different types of realtime medical data. For example, blood pressure can be sampled from monitoring devices to the client device 9 times per second. As another example, raw waveform data, e.g., ECG data obtained from chest sensors can be sampled 200 times per second. As another example, blood oxygenation obtained from finger sensors can be sampled 33 times per second. As another example, bio-impedance can be sampled 33 times per second. When multiple different sample rates are used, a buffer can be used to buffer realtime medical data. Once a particular amount of data is buffered at the buffer, the realtime medical data can be transmitted together to the client device.

The system determines a plot time of the particular waveform (Step 510). For example, based on the value of the plot time, the system can determine how long the system writes the particular waveform in the buffer determined based on the buffer information.

The system generates realtime medical data (Step 512). Based on the determinations (Steps 504-510), the system writes the particular waveform in the buffer based on the sampling rate for the plot time. In this example, the written waveform data are the requested waveform data. In some implementations, the system stores the generated realtime medical data in the database.

Figure 6:
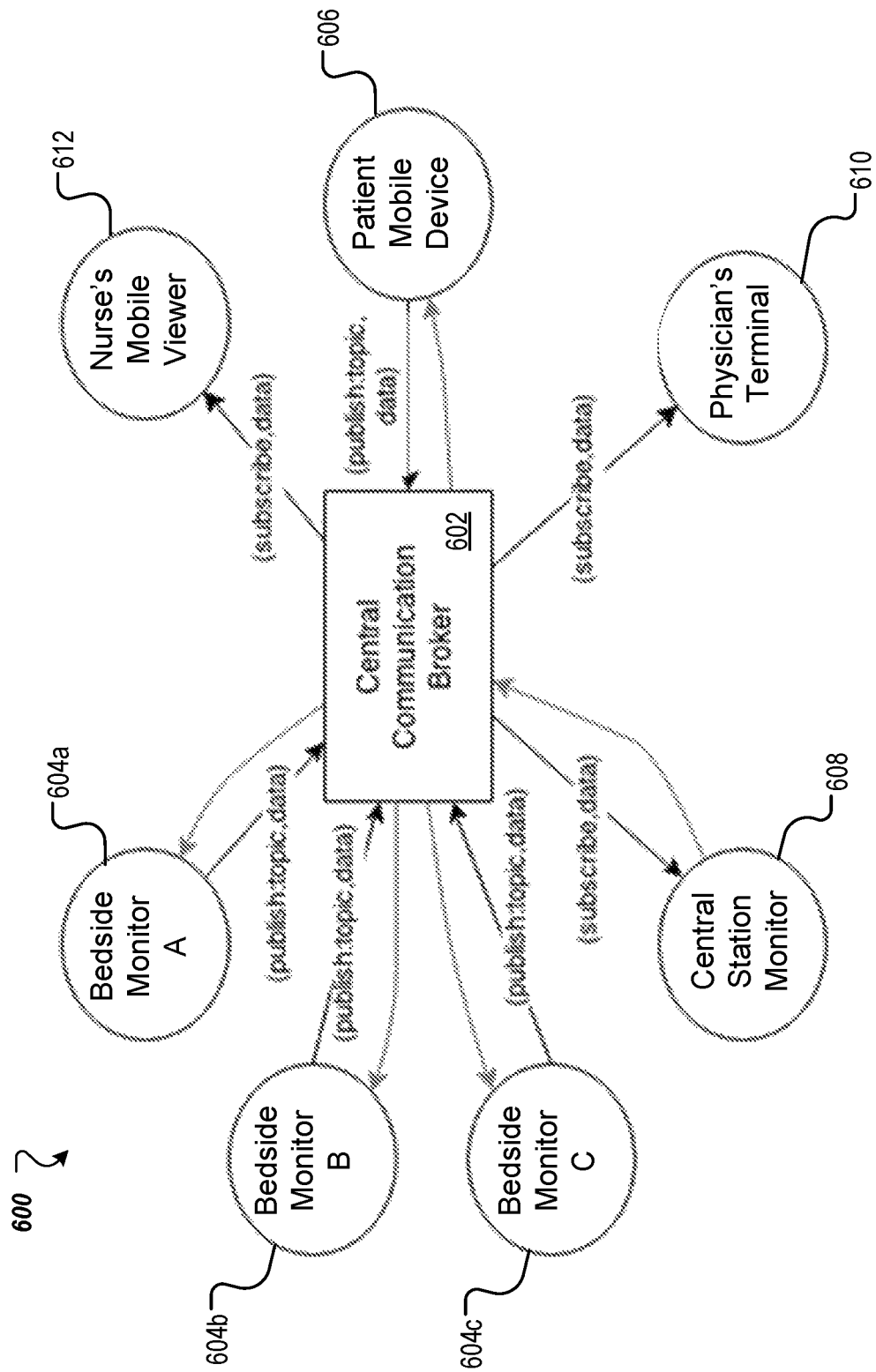
FIG. 6 is a diagram illustrating an network for facilitating a publisher/subscriber system for realtime healthcare information.

FIG. 6 is a diagram illustrating an example system 600 for implementing a publisher/subscriber protocol for allowing client devices to subscribe to various channels to receive realtime patient information. The system 600 includes a central communication broker 602 which can be, for example, the system 330 of FIG. 3, the service broker 230 of FIG. 2, or the service broker 113 of FIG. 1. The central communication broker 602 receives realtime patient information from a number of patient side devices, such as, for example, bedside monitors 604a-c. In this example, the bedside monitors 604a-c are each in communication with one or more patient worn sensors and/or other sensors that can provide realtime or near realtime data for patients, such as vital signs, orientation, sleep state, etc. The bedside monitors 604a-c can be implemented as, for example, the bedside monitor 108 of FIG. 1 or the monitoring device 250 of FIG. 2. The bedside monitors 604a-c receive realtime patient data from the one or more sensors and provide the realtime patient data to the central communication broker 602 through a network. A patient mobile device 606 also services as a source of realtime patient information for the central communication broker 602. The patient mobile device 606 can be, for example, a mobile phone or tablet belonging to or associated with a patient that has transitioned from a healthcare facility, such as a hospital, to their home or the home of a relative. The patient mobile device 606 is in wireless communication with one or more patient worn sensors and functions to aggregate data received from the patient worn sensors and transmit the data over a network, such as the Internet, to the central communication broker 602.

The central communication broker 602 can publish the information received from the bedside monitors 604a-c and patient mobile device 606 to a number of subscriber channels to allow other devices to subscribe to the channels to receive and present realtime patient data. For example, a central station monitor 608 can be in communication with the central communication broker 602 and subscribe to one or more channels published by the central communication broker 602. The central station monitor 608 perform the functions of, for example, the client device 114 of FIG. 1, the client device 210 of FIG. 2, or the client device 310 of FIG. 3. Other client devices can include a physician's terminal 610 and a nurse's mobile viewer 612 (e.g., a mobile phone belonging to or assigned to a nurse or other care giver). The physician's terminal 610 and nurse's mobile viewer 612 can be implemented to perform the functions of, for example, the client device 210 of FIG. 2 or the client device 310 of FIG. 3.

The system 600 implements a loosely coupled publish/subscribe pattern that is used for the communication between various sub-systems. The system components which send data (e.g., bedside monitors 604a-c and patient mobile device 606) will publish messages including realtime data to the central communication broker 602 on a specific topic. The system components which want to receive data associated with a specific topic (e.g., central station monitor 608, physician's terminal 610, and nurse's mobile viewer 612), subscribe to one or more specific topic channels. At the core of the communication architecture is the central communication broker 602 that aggregates, and routes messages published to specific topics to subscribers of those topics. Topics can include, for example, realtime (time sensitive) telemetry data such as waveform data, vitals, alarms, sensor functionality information, etc.

Continuing with FIG. 6, the central communication broker 602 can publish distinct channels containing realtime patient information and other patient information for different patients or different sets of patients. For example, a first channel may include relevant realtime patient information for all patients located in a particular area of a healthcare facility, such as on a particular floor of a hospital or in a particular ward. A second channel can include realtime patient information for all patients currently under the care of a particular cardiologist. This can allow that cardiologist (and other caregivers assisting the cardiologist) to subscribe to a channel that will provide information for all patients of interest to the cardiologist. A third channel can include realtime patient information for all patients within the system that are receiving a particular classification or category of treatment. For example, real time patient information for all patients receiving kidney dialysis treatment can be published on a particular channel. The central communication broker 602 can additionally publish one or more channels for each individual patient in the system.

As described above, the central communication broker 602 receives this realtime patient information from computing devices in communication with patient worn sensors (e.g., bedside monitors 604a-c and patient mobile device 606). These computing devices can be, for example, bedside monitors, or portable computing devices such as smartphones, tablets, personal computers, or the like in communication with one or more patient worn sensors. These computing devices can be, for example, the monitoring device 250 of FIG. 2. The realtime patient information is provided to the central communication broker 602 by these monitoring devices along with patient identifiers to identify patients associated with the information. Specifically, bedside monitor 604a communicates with one or more patient worn sensors monitoring one or more vital signs for a patient. The bedside monitor 604a provides the information detected by the patient worn sensors (e.g., after pre-processing of the information) to the central communication broker 602 over a communications network. The information is provided along with a unique patient identifier for the patient such that the information can be linked to the patient when provided to another end user device (e.g., physician's terminal 610) for presentation to a caregiver. The central communication broker 602 then publishes this realtime patient information that is received from the bedside monitor 604a on one or more channels. End users can then subscribe to one or more of the channels to view relevant realtime patient information. For example, the nurse's mobile viewer 612 can subscribe to a channel that includes all information for the patient associated with bedside monitor 604a by establishing a websocket connection with the central communication broker 602 and requesting information using the patient identifier for the patient associated with the bedside monitor 604a. In this manner, end user devices (such as the client device 210 of FIG. 2, the client device 310 of FIG. 2, and the client device 114 of FIG. 3) can receive realtime patient information provided by patient worn sensors without directly communicating with the patient worn sensors or the computing devices in direct communication with the patient worn sensors. Additionally, multiple subscribing devices can monitor information from the same patient simultaneously. For example, both the nurse's mobile viewer 612 and the physician's terminal 610 can subscribe to a channel published by the central communication broker 602 that includes waveform information for a patient associated with bedside monitor 604b to monitor the waveform information simultaneously.

In other words, the present system does not require an end user device, such as nurse's mobile viewer 612, to establish a direct connection with a patient side computing device, such as bedside monitors 604a-c. Rather, the end user device can receive realtime data generated by the bedside monitors 604a-c and present this realtime information to a care giver by subscribing to one or more channels published by the central communication broker 602. In this manner, the caregiver's end user device (e.g., central station monitor 608, physician's terminal 610, and nurse's mobile viewer 612) does not need to know network identities for the bedside monitors 604a-c, but rather can simply identify the channel(s) that include the desired realtime patient information and the central communication broker 602 serves as an aggregator to provide the realtime information to the caregiver's end user device. Specifically, the central communication broker 602 receives the realtime information generated by, for example, the bedside monitor 604a, associates the realtime information with a unique identifier for the patient associated with bedside monitor 604a, and then publishes the realtime information on one or more channels. The caregiver's end user device can then subscribe to one or more of the one or more channels to view the realtime information without connecting directly with the bedside monitor 604a or needing to know a network identity for the bedside monitor 604a.

In some implementations, one or more computing devices associated with a particular caregiver can subscribe to one or more realtime patient information channels published by the central communication broker 602 using a caregiver identifier (ID) for the caregiver. For example, the central station monitor 608 can use a caregiver identifier to subscribe to one or more channels containing information for the patient associated with patient mobile device 606. The caregiver identifier can be, for example, a unique alphanumeric code associated with the caregiver. In some implementations, the caregiver identifier can be used as login credentials by the caregiver to log into a device to view patient information. In some implementations, the caregiver identifier for the caregiver can be associated with one or more patient identifiers, e.g., for patients for which the caregiver is partially responsible for care (e.g., patients associated with bedside monitors 604*a-c*). For example, patient identifiers for patients that have had surgery performed by, or are scheduled to have surgery performed by a particular surgeon can be linked to a caregiver identifier for the surgeon. The caregiver's computing device (e.g., physician's terminal 610) can transmit the caregiver's unique identifier to the central communication broker 602. The central communication broker 602 can then use the received unique identifier to identify one or more channels of interest for the caregiver. For example, the central communication broker 602 can identify channels for patients having patient identifiers associated with the caregiver identifiers (e.g., as part of a caregroup) and provide those published channels to the physician's terminal 610. In this manner, the caregiver is not required to manually enter the information that he would like to view. Rather, relevant patient information is automatically provided to the caregiver's device based on the caregiver identifier for the caregiver.

As another example, an IT technician can have a unique caregiver identifier. Upon logging into a device, the technician's device can provide the unique caregiver ID to the central communication broker 602. The central communication broker 602 can then identify channels that include operational information for a number of patients (e.g., all patients within a particular facility or particular ward), such as a battery level, network connectivity status, one or more sensors coming detached, or information on the functionality of the sensor/medical devices associated with the patients (e.g., information that would be of interest to an IT worker or hospital technician). The central communication broker 602 then automatically subscribes the technicians device to those channels such that the technician can view information indicative of when a particular patient sensor may need maintenance or other attention.

As another example, a cardiologist may subscribe to a channel published by the central communication broker 602 that includes vital sign information for all patients within a cardio care group. Therefore, the physician can monitor patient information for all patients in the care group without the physician's device having to subscribe to an individual channel for each patient.

In some implementations, the central communication broker 602 will implement a set of rules for determining which information to provide to a subscribing device based on a caregiver ID. For example, the central communication broker 602 can determine that for caregiver IDs associated with physicians, only patient data for patients directly associated with the physician will be provided (e.g., not information for all patients within a ward or care facility). For caregiver IDs associated with particular supervisory nurses (e.g., nurses who may be working a central nursing station, such as central station monitor 608), information for all patients within a particular ward or healthcare facility is provided. Caregiver IDs for IT technicians will be provided with information only on sensor functionality and not actual patient vital sign data. A patient or relative of a patient will be provided with only information for that patient and not other patients (e.g., the relative's caregiver ID allows the relative to subscribe only to channel(s) associated with the patient to which the relative is related).

As an example implementation, the central communication broker 602 can require subscribing devices to specify channel subscription information in a particular format, such as by using a particular subscription pattern. On example format can require the subscribing devices to identify relevant channel information in a hierarchical manner. For example, the nurse's mobile viewer 612 can identify channel information according to hierarchy that requires the subscribing devices to identify a particular system or network, a particular patient or group of patients, and a set of information for the identified patient or patients. For example, a hierarchical request can identify a particular channel using the following nomenclature:

/system-identifier/patient-identifier/information-type

For example, using this example channel identification nomenclature, the nurse's mobile viewer 612 can subscribe to a channel for patient having a patient ID of 3202 that shows waveform data for the patient using the following channel identification format:

/Ward17/3202/waveform

Other types of information that can be requested other than waveform data can include vital sign data, alarm state data, operational data, orientation data, or specific vital signs, such as respiration rate, heart rate, blood oxygenation level, etc. Static patient information (e.g., patient treatment history) can also be provided using this nomenclature. The central communication broker 602 uses the information included in the hierarchical nomenclature to identify the appropriate channel or channels of information to provide to the subscribing device. In some implementations, the central communication broker 602 can allow for wildcard characters. For example, the system can use the symbol "#" as a multi-level wildcard character and the symbol "+" as a single level wildcard character. A multi-level wildcard character requests all information available for the indicated level in the hierarchy and all subsequent levels, while a single level wildcard character would require the user to specify lower hierarchical levels. For example, the following indicator would be a request for all patient information for patient 3202:

/Ward17/3202/#

The following indicator would be a request for all patient information for all patients in ward 17:

/Ward17/#

Continuing with this example, the following indicator would be a request for battery level information for all patients in ward 17:

/Ward17/+/battery-level

Other combinations based on this nomenclature would be ready apparent from the above examples. The data viewing application running on a subscriber device (e.g., a web browser establishing a websocket connection) can select the publisher channel topics of interest and consume data from the channel topic as desired and present data appropriately. A subscription pattern is a filter sent to the communication broker to be applied for this connection. Such a subscription service, based on patient IDs and identified information types, allows a subscriber to easily follow a patient as the patient moves through different environments, including from immediate recovery after surgery, to physical therapy, to home, without the subscribing device needing to know the location of the patient or the identity of a computing device on the patient side (such as the patient's mobile phone or a bedside monitor).

In some implementations, in addition to providing realtime patient information, the bedside monitors 604a-c and patient mobile device 606 can act as subscribing devices. For example, the user of the patient mobile device 606 can subscribe to one or more channels published by the central communication broker 602. In some implementations, devices that provide the realtime patient information (bedside monitors 604a-c and patient mobile device 606) will be automatically subscribed to one or more channels published by the central communication broker 602. For example, the bedside monitors 604a-c and patient mobile device 606 can be automatically subscribed to channels indicating alarm acknowledgements. For example, the bedside monitor 604a can provide information to the central communication broker 602 indicating an alarm state for a patient associated with the bedside monitor 604a (e.g., cardiac arrest). A caregiver that receives the alarm can acknowledge that the alarm has been received (e.g. by selecting a button or a control) to let other caregivers know that they are attending to the patient alarm state. The acknowledgement of the alarm state by the caregiver can be provided from the caregiver's device back to the central communication broker 602 and then provided on a published channel to the bedside monitor 604a.

In some implementations, there is a separate instance of the central communication broker 602 for each particular grouping of monitor devices. For example, the system 600 can implement a separate instance of central communication broker 602 for each ward in a hospital. As another example, each healthcare facility within a healthcare system can have a separate instance of the central communication broker 602. In some implementations, when a monitoring device connects to the system 600, the monitoring device can specify a specific ward to other grouping to be grouped within. For example, a user of the bedside monitor 604a can specify a particular ward with which the bedside monitor 604a is to associated upon initialization of the bedside monitor 604a. Thereafter, even when the bedside monitor 604a is moved to other physical locations, the bedside monitor 604a can continue to be associated with the originally specified ward and therefore will continue to be associated (and provide realtime patient information to) the same instance of the central communication broker 602.

In some implementations, a caregiver can request historic information from the central communication broker 602. For example, the physician can use the physician's terminal 610 to replay past data streams for the patient associated with bedside monitor 604a. The physician can specify dates and times to retrieve formerly realtime patient information from the central communication broker 602. This historic data can be provided, for example, via a websocket connection between the physician's terminal 610 and the central communication broker 602. In some implementations, the user device, such as the physician's terminal 610, may not be able to process large amounts of data at once and therefore the central communication broker 602 can break up the requested historical information into smaller segments of information before providing this information to the physician's terminal 610 for display to the physician.

Figure 7A:
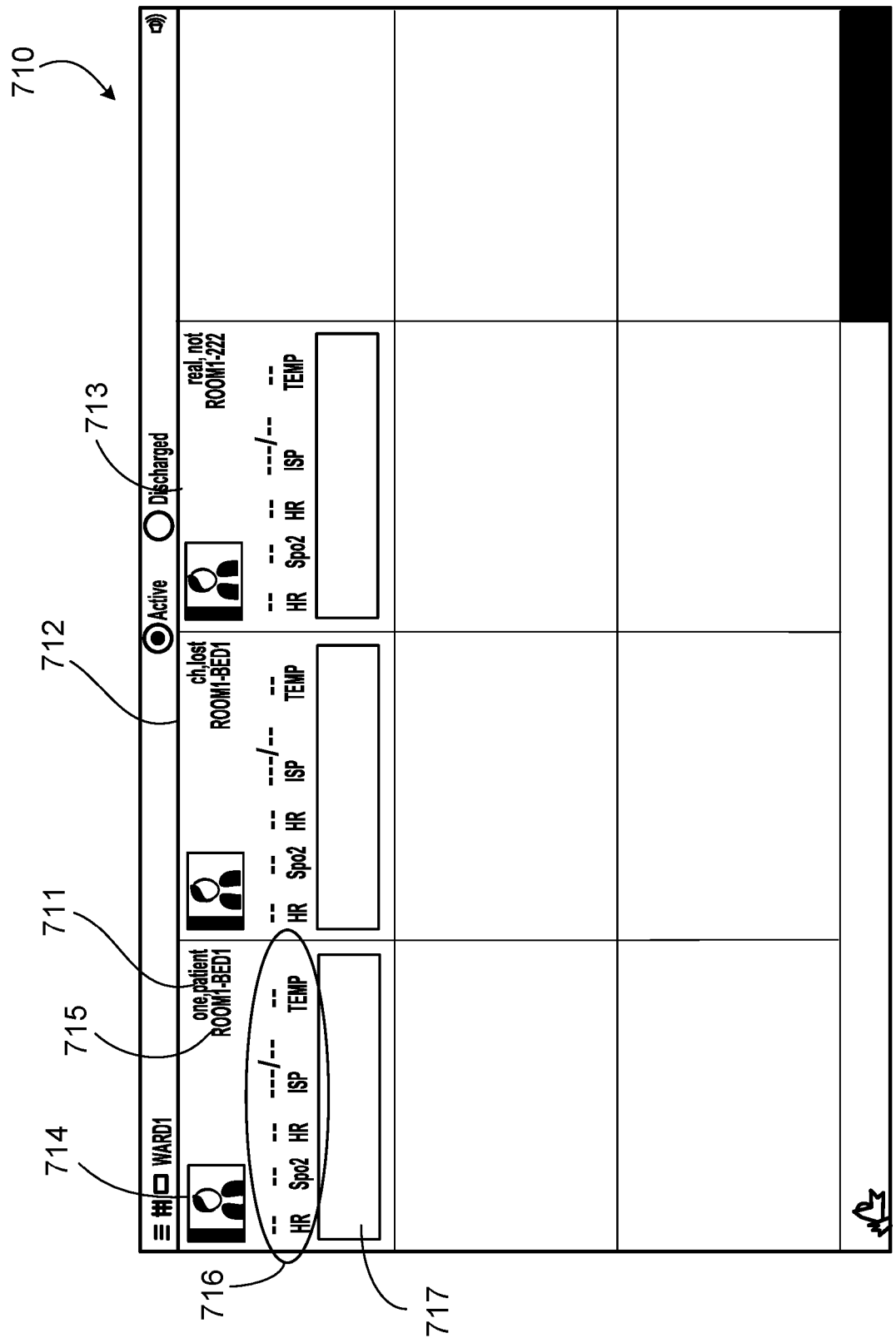
FIGS. 7A to 7D are diagrams illustrating example interfaces displayed on a client device to provide realtime medical data.

FIGS. 7A to 7D are diagrams illustrating example interfaces displayed on a client device to provide realtime medical data. FIG. 7A is a diagram illustrating an example interface 710 displayed on a client device, e.g., a laptop or a desktop device. The interface provides realtime medical data for one or more particular patients. For example, the interface 710 includes a first section 711 to provide realtime medical data for a first patient, a second section 712 to provide realtime medical data for a second patient, and a third section 713 to provide realtime medical data for a third patient. The first section 711 includes an image 714 associated with the patient, an identification code 715 to identify the patient, numeral data 716 of realtime medical data for the patient, and graphical data 717 of realtime medical data for the patient.

Figure 7B:
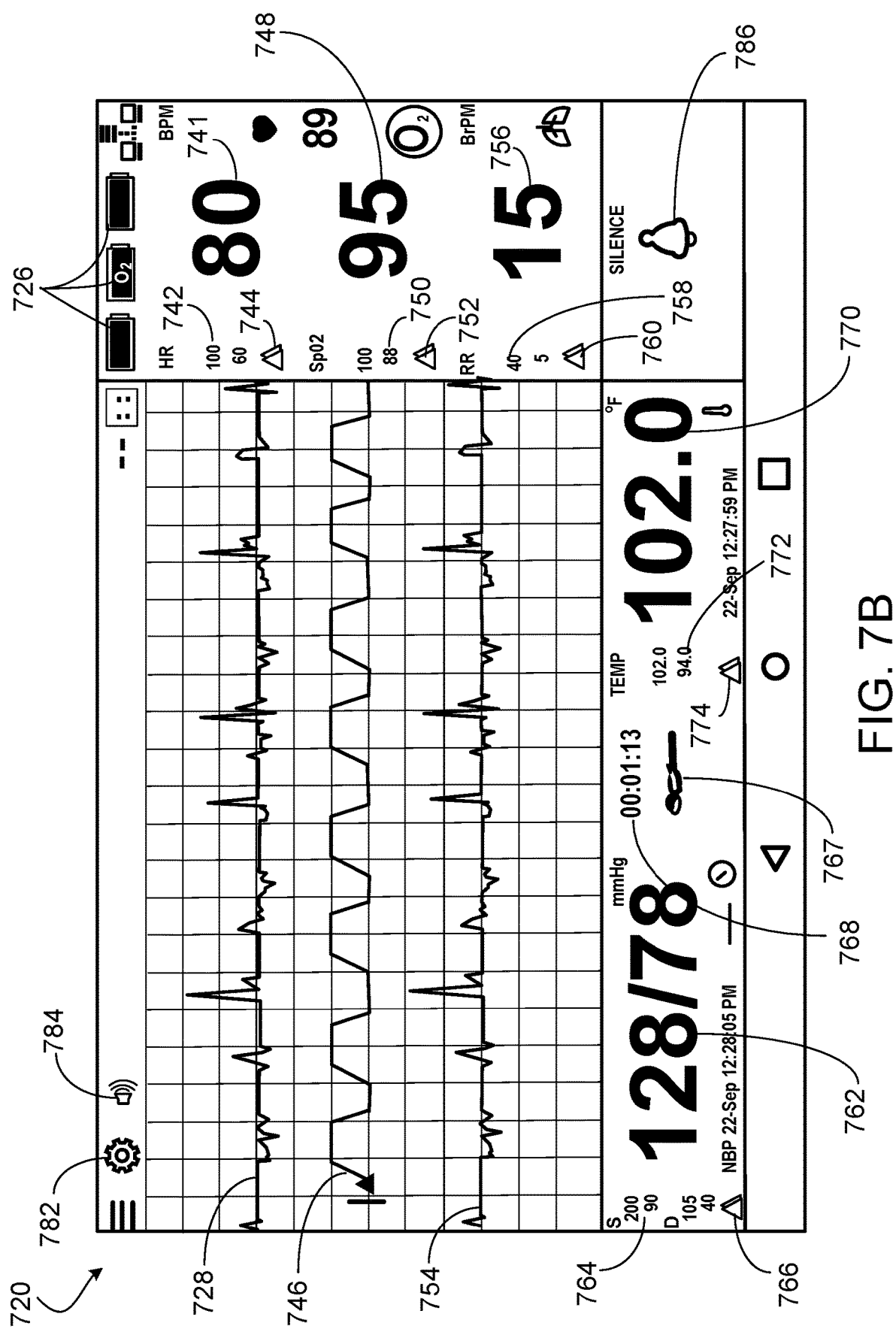

FIG. 7B is a diagram illustrating an example an example interface 720 displayed on a client device. In particular, the interface 720 provides the same or substantially similar interface provided in a monitoring device, e.g., the monitoring device 250 in FIG. 2 and/or the client device 210 in FIG. 2. The user interface 720 provides various realtime medical data for a particular patient. The user interface 720 includes icons 726 that indicate battery information for multiple sensors that are currently synced with the monitoring device. Each of the icons 726 indicates a battery charge level for each of the sensors. In some implementations, the icon 726 can also indicate a name or identifier of a sensor, such that a user can tell which sensor is associated with a particular icon. In this example, the icon 726 includes an indicator "$O_2$ to indicate that the icon 726 indicates a battery power level for a blood oxygenation sensor associated with and/or affixed to the patient. In these implementations, the requests for realtime medical data to display the icons can be provided from a client device to a service broker through an HTTP connection. The information on how the icons are to be displayed can be provided by the system (e.g., the system 330) using the HTTP connection while the realtime medical data for the icons 726 can be provided from the service broker to the client device through a websocket connection. In this manner, relatively static data that is unlikely to change is provide through the HTTP connection while the realtime medical data is provided through the websocket connection. In this particular example, the information provided via the HTTP connection can specify the positioning and shape of the battery icons while the websocket connection provides the information on the charge levels of the one or more batteries. This information (static display information from the HTTP connection, and realtime value information from the websocket connection) is then combined by the browser at the client device to display the battery icons showing the current charge level for each sensor device.

The user interface 720 additionally shows various vital sign waves and numeric levels. For example, the user interface 720 shows a heart rate waveform 728 for the patient as well as a numeric heart rate value 741 for the patient. In the example shown, the heart rate value 741 for the patient is 80 beats per minute. The user interface 720 indicates at 742 an acceptable heart rate level for the patient as falling between 60 and 100 beats per minute. Being as the current heart rate for the patient of 80 beats per minute falls within the indicated acceptable range, there is not currently an alarm state for heart rate for the patient. This is indicated by an icon 744. The icon 744 indicates whether the current heart rate of the patient is within the acceptable range or not. In a situation in which the heart rate for the patient is not within the acceptable level, the icon 744 can change to indicate an alarm state. For example, the color can change to red. Additionally, a bedside monitor can emit an audible alarm to alert nearby caregivers to an alarm state for the patient. In some implementations, other portions of the user interface 720 can flash or otherwise indicate an alarm state. For example, the displayed heart rate value 741 can flash when the patient's heart rate is outside of an acceptable level. In some implementations, the icon 744 can flash at varying rates to indicate the severity of a particular alarm state. For example, the icon 744 can flash faster the further the patient's heart rate is from the acceptable range.

In these implementations, the requests for realtime medical data to display the heart rate waveform 728, the numeric heart rate value 741, the acceptable heart rate level 742, the alarm 744 can be provided from a client device to a service broker through an HTTP connection. For example, the user of the client device can use the client device to subscribe to a published channel that includes all of the information presented on the user interface 720. The client device then receives information via the HTTP connection that specifies how the realtime information is to be displayed. For example, the information provided by the system (e.g., the system 330) to the client device (e.g., the client device 310) that is displaying the user interface 720 via the HTTP connection between the two devices can specify where on the screen certain types of information (e.g., ECG and other waveform data, 728, 746, and 754; heart rate value 741, alarm state 744, etc.) is to be displayed. The HTTP data can also disclose the manner in which the data is to be displayed, including the color of various waveforms, values, backgrounds, and borders, the size of various values (e.g., size of numbers and icons) what icons, such as alarm state icon 744 look like, fonts for numbers and letters, and other display aspects. This display information can be considered static information that is unlikely to change or will change only occasionally (e.g., when the client device requests a different set of patient information and/or subscribes to a different information channel). This static or near-static information controlling the display context of the patient information is therefore transmitted via the HTTP connection.

By contrast, the realtime medical data for that indicates the values for each piece of displayed information, including, for example, the heart rate waveform 728, the numeric heart rate value 741, and the alarm state 744 is provided from the service broker to the client device through a websocket connection. This information is dynamic in that it changes as new information is collected from the patient worn sensors. The websocket connection facilitates quick transfer of this realtime, dynamically changing data which is displayed on the user interface 720 according to the display parameters specified by the information received via the HTTP connection.

The user interface 720 also shows a blood oxygenation waveform 746 and a numeric blood oxygenation value 748 for the patient. The waveform and numeric values represent dynamic data collected at a patient monitoring device such as a patient worn sensor that is published by the service broker via the websocket connection. As described above the display characteristics of the blood oxygenation waveform 746 and the numeric blood oxygentation value 748 are defined by data provided to the client device by the system via the HTTP connection. The user interface 720 also shows, at 750, an acceptable blood oxygenation range for the patient. The user interface 720 further includes an alarm state icon 752 indicating that the blood oxygenation level for the patient is within the acceptable range. As described above, the information on how to display this alarm state icon 752 is provided by the HTTP connection while the state of the alarm state icon 752 (e.g., an indication of an alarm state or no alarm state) is based on dynamic information received via the websocket connection.

The user interface 720 additionally includes a respiratory rate waveform 754 and a numeric respiratory rate value 756 which shows a numeric value indicating the number of breaths per minute taken by the patient. As with the above described patient data, the waveform and numeric values represent dynamic data collected at a patient monitoring device such as a patient worn sensor. This dynamic data is published by the service broker via the websocket connection with the client device. As described above the display characteristics of the respiratory rate waveform 754 and the numeric respiratory rate value 756 are defined by data provided to the client device by the system via the HTTP connection. In the example shown, the patient has a respiration rate of 15 breaths per minute, as indicated by the respiratory rate value 756. The user interface 720 also shows, at 758, an acceptable respiration rate range for the patient. In the example shown, the acceptable respiration rate range is 8 breaths per minute to 40 breaths per minute. The user interface 720 further includes an alarm state icon 760 indicating that the respiration rate for the patent is within the acceptable range. As described above, the information on how to display this alarm state icon 760 is provided by the HTTP connection while the state of the alarm state icon 760 (e.g., an indication of an alarm state or no alarm state) is based on dynamic information received via the websocket connection.

The user interface 720 further includes a blood pressure value 762 for the patient. In the example shown, the blood pressure value 762 indicates that the patient's current blood pressure is 128/78. The user interface 720 additionally includes, at 764, an acceptable blood pressure range for the patient. As described above, information dictating the nature of how the blood pressure value 762 is displayed is provided via the HTTP connection between the system and the client device. This information can include, for example, the size, font, positioning, and color of the displayed blood pressure value 762. The value of the blood pressure value 762 is dynamic information provided by the service broker to the client device via the websocket connection.

The user interface 720 further includes an alarm state icon 766 indicating that the blood pressure for the patent is within the acceptable range. Once again, different display characteristics for the alarm state icon 766 can be defined by information received via the HTTP connection. For example, the information received via the HTTP connection can indicate several possible alarm state icons 766 for indicating different alarm states. The information indicating which alarm state icon 766 to display is dynamic information received via the websocket connection.

The user interface 720 further includes an orientation indicator 767 indicating a current orientation for the patient and a time indicator 768 indicating how long the patient has been in the current orientation. The orientation indicator 768 can help a caregiver to identify if the patient has been in a current orientation for longer than a preferred length of time. The orientation indicator 768 can also be used to indicate that the patient has fallen and is in need of assistance (e.g., through use of an audible or visual alarm, indicating that the alarm is "off"). The client device can receive a number of orientation indicators 767 via the HTTP connection, with each variation of the orientation indicator 767 indicating a different orientation for the patient (e.g., supine, prone, laying on one side or the other, semi-inclined, sitting upright, standing, etc.). The client device can receive dynamic information via the websocket connection that indicates an orientation for the patient and the client device can then use that dynamic information received via the websocket connection to determine which of the orientation indicators 767 received via the HTTP connection to display. In other words, the information received via the HTTP connection defines how information indicating a particular orientation is displayed while the information received via the websocket connection indicates the orientation of the patient and therefore determines which previously received orientation indicator 767 is displayed.

The user interface 720 further includes a numeric body temperature value 770 for the patient. In the example shown, the body temperature value 770 indicates that the patient's temperature is currently 102.0 degrees Fahrenheit. The user interface 720 also includes, at 772, an acceptable temperature range for the patient, and an alarm state icon 774 indicating whether or not the body temperature for the patent is within the acceptable range. As described above, information dictating the nature of how the body temperature value 770 is displayed is provided via the HTTP connection between the system and the client device. This information can include, for example, the size, font, positioning, and color of the displayed body temperature value 770. The value of the body temperature value 770 is dynamic information provided by the service broker to the client device via the websocket connection. Once again, different display characteristics for the alarm state icon 774 can be defined by information received via the HTTP connection. For example, the information received via the HTTP connection can indicate several possible alarm state icons 774 for indicating different alarm states. The information indicating which alarm state icon 774 to display is dynamic information received via the websocket connection.

The user interface 720 further includes control buttons 782, 784, and 776. The control button 782 is used for accessing various controls or other display screens for one or more other monitoring devices. For example, the control button 782 can be used to access additional information about the system, the monitoring devices (e.g., patient worn sensors or a bedside monitor), or the patient. As another example, the control button 782 can be used to access a settings menu. The settings menu can be used to, for example, change the brightness of the display of the monitoring device. The volume control button 784 allows a user to change the volume of audible alarms. The control button 786 allows a user to mute all the alarms describe above. In some implementations, the control button 786 can mute particular alarms based on user settings. The display characteristics and actions performed response to user interaction with the control buttons 782, 784, and 776 can be defined by information received via the HTTP connection as the functions performed in accordance with the control buttons 782, 784, and 776 is generally static in nature and not directly related to realtime data received from one or more patient sensors.

In some implementations, the user interface 720 can include additional static and/or dynamic information associated with the patient and/or with sensors associated with the patient. For example, the user interface 720 can additionally include a name or other identifier for the patient and a picture of the patient. The user interface 720 may also include information on recent or scheduled medical procedures for the patient. The user interface 720 may also include information on the patient's medical history or recently experienced medical conditions. Such information is generally considered static or relatively static in nature and can therefore be provide via the HTTP connection. In some implementations, such patient specific information can be provided via the websocket connection as the information is patient specific and considered sensitive.

In other examples (not depicted) the user interface 720 can have different display characteristics. These different display characteristics can be defined by information received via the HTTP connection. The user interface 720 may be changed for a number of reasons. For example, a different user having different information access permissions may only be able to access a subset of the information shown in FIG. 7B. Therefore, the user interface 720 may be changed to display only the information that this particular user is allowed to access. As another example, a user may wish to selectively change which information is displayed, e.g., by requesting a subset of the information shown in FIG. 7B and/or by subscribing to a different channel that includes more, less, or different information than that shown in the example in FIG. 7B. For example, a physical therapist may only be concerned with heart rate and patient orientation information. The physical therapist can subscribe to a published channel that provides only this information for a patient.

When subscribing to the channel, the client device establishes an HTTP connection with the system (e.g., the system 330). The client device can specify which information is being requested (or which channel is being requested) via the HTTP connection. The system can then provide information for how to display that requested information via the HTTP connection. The service broker then provides the realtime values for the desired information via the websocket connection. The client device can then display only the requested information types as specified by the HTTP information having the values specified by the websocket information. In this way, by subscribing to a different channel (or requesting a different set of patient information), the client device receives updated information via the HTTP connection that specifies how this new subset of information is to be display by the user interface 720. In this example, the HTTP information may, for example, specify that patient heartrate information is displayed along a top half of the screen while patient orientation information is displayed along the bottom of the screen. It should be recognized that any combination of the above described information can be requested and displayed and that the different display formats/layouts are defined by the information received via the HTTP connection while the values for displayed information are received via the websocket connection.

Figure 7C:
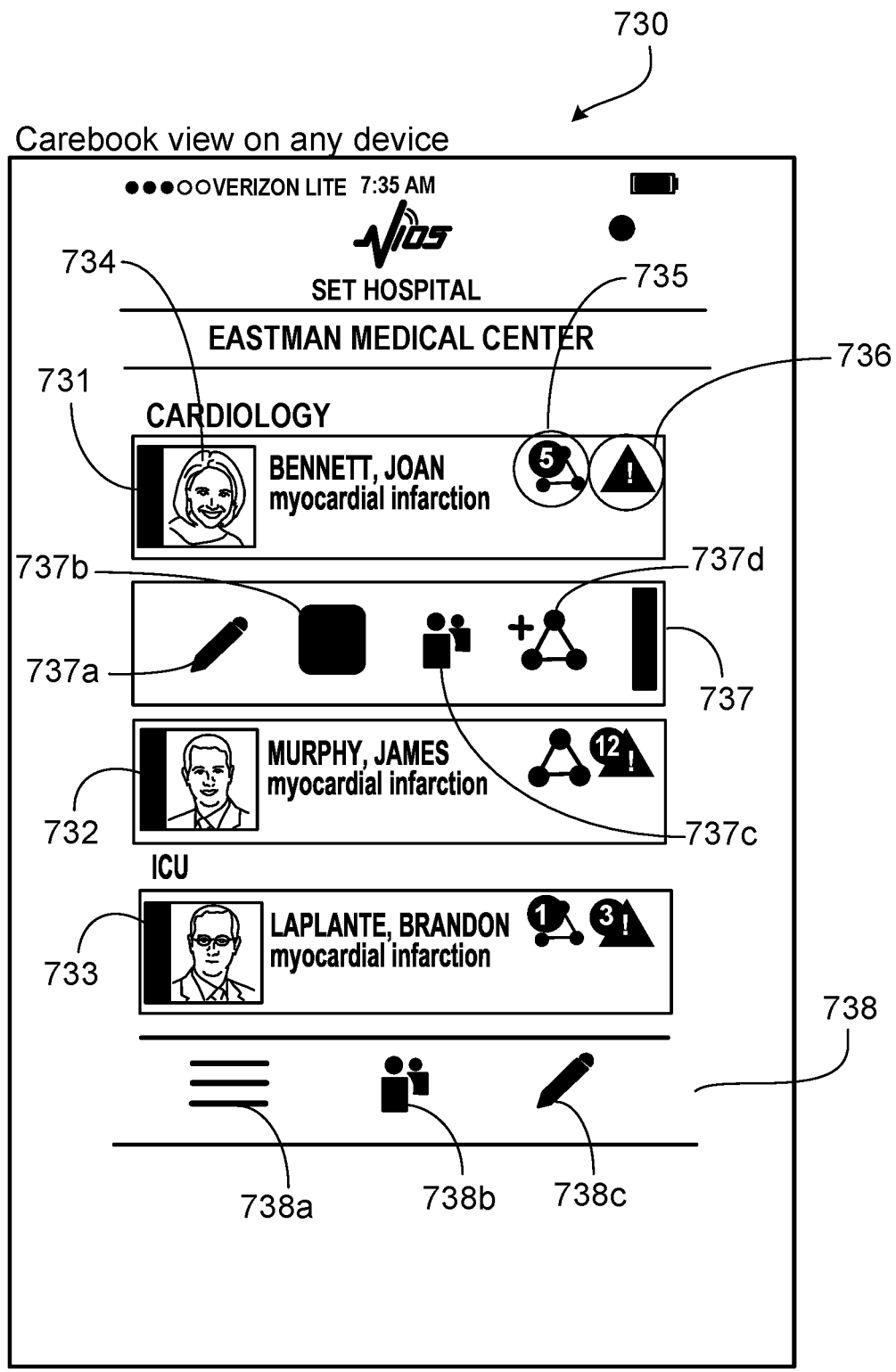

FIG. 7C is a diagram illustrating an example an example interface 730 displayed on a client device. For example, the user interface 730 may be a user interface for a mobile device having a limited display screen area, such as a smartphone, while the user interface 720 may be a user interface for a computing device having a larger display screen such as a laptop computer, desktop computer, specialized nursing station, or tablet device. The interface provides realtime medical data for one or more patients. For example, the interface 730 includes a first section 731 to provide realtime medical data for a first patient, a second section 732 to provide realtime medical data for a second patient, and a third section 733 to provide realtime medical data for a third patient. The first section 731 includes an image 734 associated with the patient, one or more icons, e.g., icons 735 and 736, to indicate the medical status of the patient. For example, the icon 735 indicates a number of new notifications on a newsfeed for the patient indicated in section 731. The icon 736 indicates an alarm condition for the patient indicated in section 731, for example, the patient may have fallen, may have an irregular heartbeat, or may have missed a scheduled medication dosage. In some implementations, a section 737 displaying icons 737*a*-737*d* can be displayed in the interface 730. Selection of icon 737*a* can allow the caregiver using the user interface 730 to write a private message to the patient indicated in section 731. Selection of icon 737*b* can allow the caregiver using the user interface 730 to send a message to other caregivers in the care group for the patient. Selection of icon 737c can cause a list or other visual representation of caregivers in a care group for the patient indicated in section 731 to be displayed. Selection of icon 737d can allow the caregiver using the user interface 730 to post a message to a "wall" for the patient indicated in section 731 that can be viewed by all or a subset of the caregivers for the patient.

In some implementations, the user interface 730 additionally includes a section 738. The section 738 shows a control button 738a to allow a user of the mobile device to access additional information and control menus. For example, the control button 738a allows the user to access a menu screen. The menu screen can allow the user to access additional information, change settings, or indicate alert preferences, or viewing preferences. For example, the user can select the control button 738a to cause the mobile device to display a settings screen or other menu screen. The user can select icon 738b to see a list of caregroup members. For example, selection of icon 738b can cause the user interface 730 to display a list of patients for whom the user is an associated caregiver. As another example, selection of icon 738b can cause the user interface 730 to display a list of caregivers that are part of one or more particular caregiver groups that the user is a member (e.g., a list of all caregivers in a radiology caregiver group). The user can select icon 738c to write a message to another user of the application, such as another caregiver or a patient.

Figure 7D:
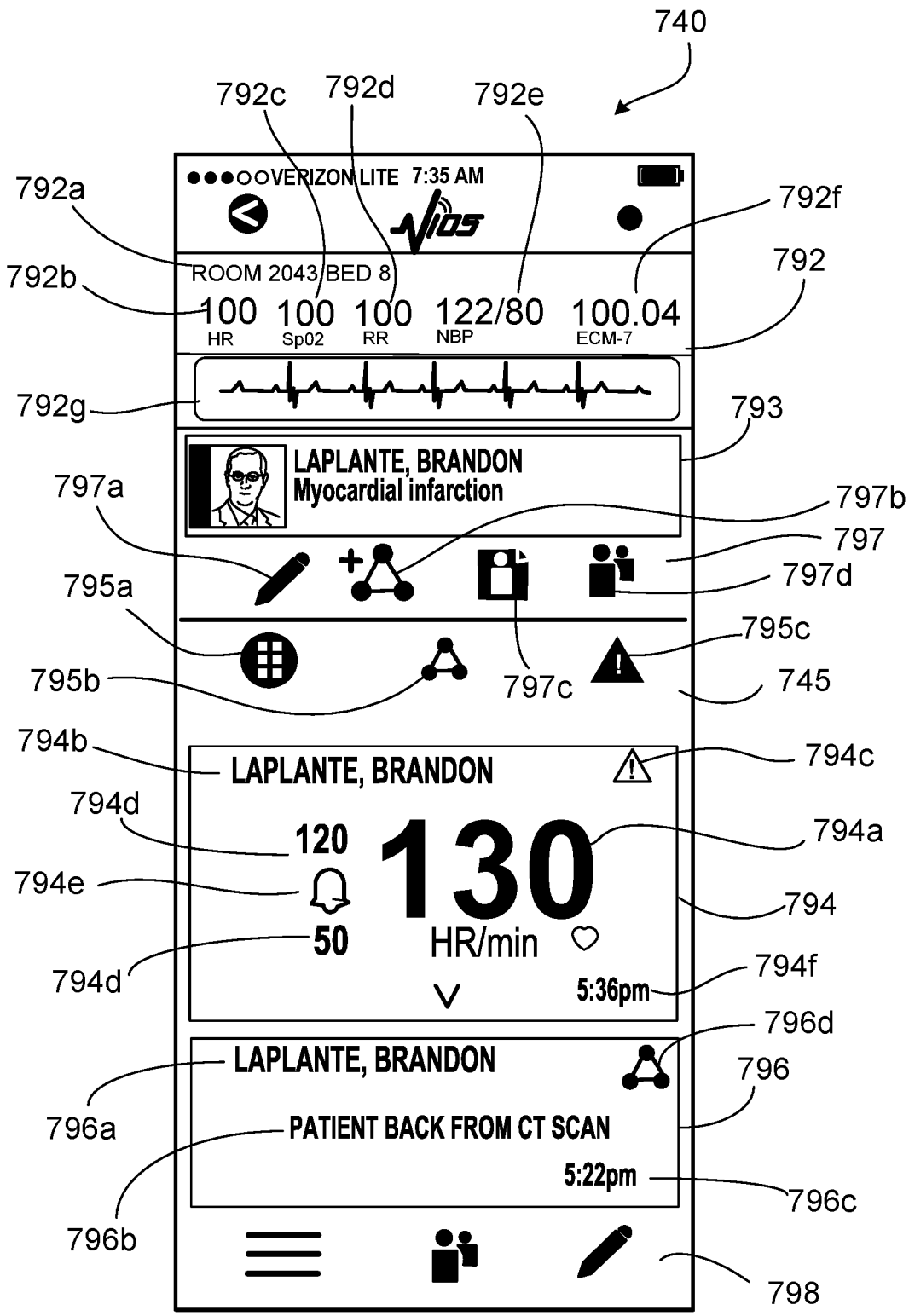

FIG. 7D is a diagram illustrating an example an example interface 740 displayed on a client device. For example, the interface 740 can be displayed on a mobile device having a limited display screen area such as a smartphone or a tablet. In some implementations, the user interface 740 can be a user interface 730 presented in response to a user selection of the section 733 in the user interface 730 described above with reference to FIG. 7C. Referring back to FIG. 7D, the interface 740 provides realtime medical data for a particular patient.

The user interface 740 includes a section 792 comprising multiple areas 792a-792g to provide various realtime medical data. The area 792a indicates that the patient is located in bed 8 of room 2043 of a healthcare facility. The area 792b indicates a numeric heart rate value for the patient. In the example shown, the heart rate value is 100 beats per minute. The area 792c indicates a numeric blood oxygenation value for the patient. The area 792d indicates a numeric respiratory rate value for the patient. In this example, the respiratory value is 100 breaths per minute. The area 792e indicates a blood pressure value for the patient. In the example shown, the patient's current blood pressure is 122/80. The area 792f indicates a numeric body temperature value for the patient. In the example shown, the patient's temperature is currently 100.04 degrees Fahrenheit. The area 792g indicates various vital sign waves. In some implementations, the area 792g can display one type of vital sign wave. For example, the area 792g can display a heart rate waveform. In some implementations, the area 792g can display multiple types of vital sign waves. For example, the area 792g can display a heart rate waveform as well as a respiratory rate waveform. As described above with respect to FIG. 7B, the information shown in the user interface 740 can be a combination of information received via the HTTP connection and the websocket connection. For example, the nature of how the information that is displayed and what information is to be displayed can be specified by information received via the HTTP connection. The values for this displayed information are specified by dynamic data received via the websocket connection.

The user interface 740 includes a section 793 that displays patient information. For example, the section can display a photo showing the patient and the patient's name. In some implementations, the section 793 further indicates information about the patient's symptom or disease. In some implementations, the patient information is transferred between the client device and the service broker through an HTTP connection as this information is generally static data.

Selection of icon 795a can cause the user interface 740 to display a carefeed and alarm history for the patient. The carefeed can include, for example, messages posted by the patient and/or caregivers associated with the patient; historical medical information for the patient (including historical vital sign information), and past alarm states for the patient, the nature of those alarm states, and actions taken to respond to those alarm states. Selection of icon 795b can cause only the carefeed to be displayed without the list of alarms. Selection of icon 795c can cause the list of alarms to be displayed without the other carefeed information.

The user interface 740 includes a section 794 that display various realtime medical data for the patient. The section 794 provides more detailed realtime medical data than the section 792. In some implementations, when a user selects a particular area of the section 792, the user interface 740 displays realtime medical data related to the particular area in the section 794. For example, when a user selects the area 792b that is related to a heart rate value, the section 794 provides detailed realtime medical data related to a heart rate value of the patient. In particular, the section 794 includes multiple areas and icons 794a-794g to display detailed realtime medical data related to a heart rate value of the patient. The area 794a displays a current heart rate value of the patient. The area 794b displays the name of the patient. The icon 794c indicates that there is currently an active alarm for the patient that has not yet been addressed by the caregiver. In some implementations, selection of the alarm 794c can cause additional details about the alarm state to be displayed. In some implementations, the icon 794c can be color coded or have another visual indicator (such as blinking at a particular pace) to indicate a relative severity of the alarm condition for the patient. The area 794d displays an acceptable heart rate level for the patient as falling between 50 and 120 beats per minute. Being as the current heart rate for the patient of 130 beats per minute falls within the indicated acceptable range, there is currently an alarm state for heart rate for the patient. This is indicated by an icon 794e. The icon 794e indicates whether the current heart rate of the patient is within the acceptable range or not. In a situation in which the heart rate for the patient is not within the acceptable level, the icon 794e can change to indicate an alarm state. For example, the icon 794e can change the color. As another example the icon 794e can flash when the patient's heart rate is outside of an acceptable level. In some implementations, the icon 794e can flash at varying rates to indicate the severity of a particular alarm state. For example, the icon 744 can flash faster the further the patient's heart rate is from the acceptable range. The area 794f displays the time at which the a high heartrate alarm state was first detected. As described above, the information shown in section 794 can be a combination of information received via the HTTP connection and the websocket connection. For example, the nature of how the information that is displayed and what information is to be displayed can be specified by information received via the HTTP connection. The values for this displayed information are specified by dynamic data received via the websocket connection.

The section 796 provides one or more activities of the patient. In some implementations, the area 796a provides the name of the patient. The area 796b displays a recent activity of the patient. For example, if the patient recently had a CT scan, the area 796b can indicate that the patient had a CT scan. The section 796 can additionally provide time information. That is, the area 796c can display the time at which the patient's activity was reported to the system or the time at which the patient performed the activity. The section 796 can additionally include an icon 796d allowing a user to share the information about the patient's activity with other users, e.g., hospital personnel, family of the patient, or caregivers. In these implementations, the patient information including the patient's name can be transferred between the client device and the service broker through an HTTP connection while realtime medical data including a patent's activity and a time stamp can be updated asynchronously between the client device and the service broker through a websocket connection.

In some implementations, patent information displayed in the section 793 and 796 can be static while realtime medical data displayed in the sections 792, 794, and 796 can be continually updated by the service broker. For example, the realtime medical data displayed in the section 792 and 794 and the patient's activity and the time stamp displayed in the section 796 can be asynchronously updated by the service broker through a websocket connection. On the other hand, the static patient information displayed in the section 793 and the patient's name displayed in the section 796 can be provided through an HTTP connection. The service broker does not update this patent information asynchronously. Thus, realtime medical data can be efficiently updated using a websocket connection. By using two different types of connections, the system can manage patient information and realtime medical data efficiently.

Other information that can be displayed as part of one or more of the user interfaces shown in FIGS. 7A-7D can include an instantaneous wellness score/index for each patient. For example, for each vital parameter, the system can identify a clinical range for the parameter and indicate, for each vital sign, how close to being within the clinical range the patient is on a scale of, for example, 1-10 or 0-5. For example an instantaneous wellness score of 0 can indicate that a particular vital sign for the patient is within the optimum range (doing well) and 5 can indicate that the vital sign is significantly out of range (very poor). This wellness score template may be configured for each clinical setting. Additionally, a single wellness score based on all vital signs can be calculated for the patient. The wellness score may be computed by considering the parameter value and the corresponding score. The aggregate score can represent a wellness index (e.g., 0-2 means good, 3-5 means not good). A trend of the wellness score viewed over a period of time can indicate to a caregiver the overall health status of the patient for a given time period.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communications network. Examples of communications networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. For example, the subject matter is described in context of scientific papers. The subject matter can apply to other indexed work that adds depth aspect to a search. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing can be advantageous.

What is claimed is:

1. A method, comprising:
   receiving, by a service broker from a client device through a Hypertext Transfer Protocol (HTTP) connection, a first request for a web page, the first request including patient information for a particular patient;
   in response to the first request, determining, by the service broker, a particular web page based on the patient information for the particular patient, the particular web page displaying a first user interface;
   providing, by the service broker to the client device through the HTTP connection, the particular web page to establish a websocket connection between the service broker and the client device;
   establishing the websocket connection between the service broker and the client device;
   receiving, by the service broker from the client device through the websocket connection, a second request for first real time medical data, the second request identifying a medical data protocol that defines one or more data attributes for the first real time medical data;
   obtaining, by the service broker from one or more data sources, a first set of real time medical data samples that includes respective values of the one or more attributes for the first real time medical data;
   generating the first real time medical data based on the values of the one or more data attributes for the first real time medical data; and
   providing, by the service broker to the client device through the websocket connection, a second user interface to present the first real time medical data.

2. The method of claim 1, wherein, in response to loading the particular web page on the client device, the particular web page is configured to invoke the client device to establish the websocket connection between the client device and the service broker.

3. The method of claim 1, wherein establishing the websocket connection between the service broker and the client device comprises:

receiving, by the service broker from the client device, a websocket connection request that is invoked in response to loading the particular web page on the client device; and in response to the websocket connection request, providing, by the service broker to the client device a websocket connection response to establish the websocket connection between the service broker and the client device.

4. The method of claim 1, further comprising:
pushing, by the service broker to the client device, medical data asynchronously through the web socket connection.

5. The method of claim 1, wherein the one or more data attributes defined in the medical data protocol include at least one of an identification, a sample rate, a plot time, and buffer information.

6. The method of claim 4, wherein generating the first real time medical data based on the values of the values of the one or more data attributes for the first real time medical data comprises:
identifying, by the service broker, respective values for an identification, a sample rate, a plot time, and buffer information from the second request including the respective values of the one or more data attributes for the first real time medical data,
based on the value of the identification, determining a particular waveform of one or more waveforms that are monitored by a monitoring device in real time,
based on the respective values of the plot time, the sample rate, and the buffer information, writing, by the service broker, the particular waveform in a buffer using the sampling rate for the plot time, and
based on the particular waveform written in the buffer, generating, by the service broker, the first real time medical data.

7. The method of claim 6, wherein providing the first real time medical data comprises:
reading, by the service broker, the first real time medical data stored in the database, and
providing, by the service broker to the client device, the first real time medical data through the websocket connection.

8. The method of claim 1, wherein the client device is a subscriber to the service broker for medical data.

9. The method of claim 1, wherein the web socket connection is established between the service broker and the client device using communications based on Hypertext Markup Language (HTML).

10. The method of claim 1, wherein the particular web page simultaneously displays (i) the first user interface provided from the service broker to the client device through the HTTP connection and (ii) the second user interface that presents the first real time medical data provided from the service broker to the client device through the websocket connection.

11. The method of claim 10, further comprising:
receiving, by the service broker from the client device through the websocket connection, a third request for second real time medical data, the third request including respective values of the one or more data attributes for the second real time medical data;
receiving, by the service broker from the one or more data sources, a second set of real time medical data samples;
generating the second real time medical data from the second set of real time medical data samples based on the values of the one or more data attributes for the second real time medical data; and
updating, by the service broker, the second user interface to present the second real time medical data instead of the first real time medical data while maintaining the first user interface.

12. A system comprising: one or more computers and one or more storage devices on which are stored instructions that are operable, when executed by the one or more computers, to cause the one or more computers to perform operations comprising:
receiving, by a service broker from a client device through a Hypertext Transfer Protocol (HTTP) connection, a first request for a web page, the first request including patient information for a particular patient;
in response to the first request, determining, by the service broker, a particular web page based on the patient information for the particular patient, the particular web page displaying a first user interface;
providing, by the service broker to the client device through the HTTP connection, the particular web page to establish a websocket connection between the service broker and the client device;
establishing the websocket connection between the service broker and the client device;
receiving, by the service broker from the client device through the websocket connection, a second request for first real time medical data, the second request identifying a medical data protocol that defines one or more data attributes for the first real time medical data;
obtaining, by the service broker from one or more data sources, a first set of real time medical data samples that includes respective values of the one or more attributes for the first real time medical data;
generating the first real time medical data based on the values of the one or more data attributes for the first real time medical data; and
providing, by the service broker to the client device through the websocket connection, a second user interface to present the first real time medical data.

13. The system of claim 12, wherein, in response to loading the particular web page on the client device, the particular web page is configured to invoke the client device to establish the websocket connection between the client device and the service broker.

14. The system of claim 12, wherein establishing the websocket connection between the service broker and the client device comprises:
receiving, by the service broker from the client device, a websocket connection request that is invoked in response to loading the particular web page on the client device; and
in response to the websocket connection request, providing, by the service broker to the client device a websocket connection response to establish the websocket connection between the service broker and the client device.

15. The system of claim 12, wherein the one or more data attributes defined in the medical data protocol include at least one of an identification, a sample rate, a plot time, and buffer information.

16. The system of claim 15, wherein generating the first real time medical data based on the values of the values of the one or more data attributes for the first real time medical data comprises:
identifying, by the service broker, respective values for an identification, a sample rate, a plot time, and buffer information from the second request including the respective values of the one or more data attributes for the first real time medical data,
based on the value of the identification, determining a particular waveform of one or more waveforms that are monitored by a monitoring device in real time,
based on the respective values of the plot time, the sample rate, and the buffer information, writing, by the service broker, the particular waveform in a buffer using the sampling rate for the plot time, and
based on the particular waveform written in the buffer, generating, by the service broker, the first real time medical data.

17. The system of claim 12, wherein the particular web page simultaneously displays (i) the first user interface provided from the service broker to the client device through the HTTP connection and (ii) the second user interface that presents the first real time medical data provided from the service broker to the client device through the websocket connection.

18. The System of claim 17, the operations further comprising:
receiving, by the service broker from the client device through the websocket connection, a third request for second real time medical data, the third request including respective values of the one or more data attributes for the second real time medical data;
receiving, by the service broker from the one or more data sources, a second set of real time medical data samples;
generating the second real time medical data from the second set of real time medical data samples based on the values of the one or more data attributes for the second real time medical data; and
updating, by the service broker, the second user interface to present the second real time medical data instead of the first real time medical data while maintaining the first user interface.

19. One or more non-transitory storage devices storing instructions that are operable, when executed by one or more computers, to cause the one or more computers to perform operations comprising:
receiving, by a service broker from a client device through a Hypertext Transfer Protocol (HTTP) connection, a first request for a web page, the first request including patient information for a particular patient;
in response to the first request, determining, by the service broker, a particular web page based on the patient information for the particular patient, the particular web page displaying a first user interface;
providing, by the service broker to the client device through the HTTP connection, the particular web page to establish a websocket connection between the service broker and the client device;
establishing the websocket connection between the service broker and the client device;
receiving, by the service broker from the client device through the websocket connection, a second request for first real time medical data, the second request identifying a medical data protocol that defines one or more data attributes for the first real time medical data;
obtaining, by the service broker from one or more data sources, a first set of real time medical data samples that includes respective values of the one or more attributes for the first real time medical data;
generating the first real time medical data based on the values of the one or more data attributes for the first real time medical data; and
providing, by the service broker to the client device through the websocket connection, a second user interface to present the first real time medical data.

20. The one or more non-transitory storage devices of claim 19, wherein, in response to loading the particular web page on the client device, the particular web page is configured to invoke the client device to establish the websocket connection between the client device and the service broker.

* * * * *